United States Patent [19]
Langmore et al.

[11] Patent Number: 6,117,634
[45] Date of Patent: *Sep. 12, 2000

[54] NUCLEIC ACID SEQUENCING AND MAPPING

[75] Inventors: John P. Langmore; Vladimir L. Markarov, both of Ann Arbor, Mich.

[73] Assignee: The Reagents of the University of Michigan, Ann Arbor, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/811,804

[22] Filed: Mar. 6, 1997

[51] Int. Cl.[7] .............................. C12Q 1/68; C12P 19/34
[52] U.S. Cl. .............................................. 435/6; 435/91.2
[58] Field of Search .................... 435/6, 91.2; 935/77, 935/78

[56] References Cited

U.S. PATENT DOCUMENTS

| | | | |
|---|---|---|---|
| 4,942,124 | 7/1990 | Church | 435/6 |
| 4,962,020 | 10/1990 | Tabor et al. | 435/6 |
| 5,112,736 | 5/1992 | Caldwell et al. | 435/6 |
| 5,149,625 | 9/1992 | Church et al. | 435/6 |
| 5,308,751 | 5/1994 | Ohkawa et al. | 435/6 |
| 5,418,149 | 5/1995 | Gelfand et al. | 435/91.2 |
| 5,489,508 | 2/1996 | West et al. | 435/6 |
| 5,503,980 | 4/1996 | Cantor | 435/6 |
| 5,506,100 | 4/1996 | Surzycki et al. | 435/6 |
| 5,552,278 | 9/1996 | Brenner | 435/6 |
| 5,599,675 | 2/1997 | Brenner | 435/6 |
| 5,604,098 | 2/1997 | Mead et al. | 435/6 |
| 5,645,986 | 7/1997 | West et al. | 435/6 |
| 5,648,215 | 7/1997 | West et al. | 435/6 |
| 5,686,245 | 11/1997 | West et al. | 435/6 |
| 5,686,306 | 11/1997 | West et al. | 435/346 |
| 5,693,474 | 12/1997 | Shay et al. | 435/6 |
| 5,693,613 | 12/1997 | Shay et al. | 435/6 |
| 5,695,932 | 12/1997 | West et al. | 435/6 |
| 5,707,795 | 1/1998 | West et al. | 435/5 |
| 5,714,318 | 2/1998 | Sagner et al. | 435/6 |
| 5,714,330 | 2/1998 | Brenner et al. | 435/6 |
| 5,741,677 | 4/1998 | Kozlowski et al. | 435/91.2 |
| 5,750,341 | 5/1998 | Macevicz | 435/6 |

FOREIGN PATENT DOCUMENTS

| | | |
|---|---|---|
| 0 415 755 A2 | 3/1991 | European Pat. Off. . |
| 0 439 182 A2 | 7/1991 | European Pat. Off. . |
| 0 415 755 A3 | 8/1991 | European Pat. Off. . |
| 0 439 182 A3 | 10/1991 | European Pat. Off. . |
| 0 497 272 A1 | 8/1992 | European Pat. Off. . |
| 0 608 737 A1 | 1/1994 | European Pat. Off. . |
| 0 684 315 A1 | 3/1995 | European Pat. Off. . |
| 0 497 272 B1 | 10/1995 | European Pat. Off. . |
| 0 415 755 B1 | 12/1995 | European Pat. Off. . |
| 0 439 182 B1 | 4/1996 | European Pat. Off. . |
| WO 86/07612 | 12/1986 | WIPO . |
| WO 90/13666 | 11/1990 | WIPO . |
| WO 93/02212 | 2/1993 | WIPO . |
| WO 93/21340 | 10/1993 | WIPO . |
| WO 93/24654 | 12/1993 | WIPO . |
| WO 94/24313 | 10/1994 | WIPO . |
| WO 95/06752 | 3/1995 | WIPO . |
| WO 96/32504 | 10/1996 | WIPO . |
| WO 97/03210 | 1/1997 | WIPO . |
| WO 98/15644 | 4/1998 | WIPO . |
| WO 98/15652 | 4/1998 | WIPO . |

OTHER PUBLICATIONS

Cullman et al, Biotechniques 15(4): 578–79, 1993.
Broude et al., "Enhanced DNA sequencing by hybridization," *Proc. Natl. Acad. Sci. USA*, 91:3072–3076, Apr., 1994.
Fu et al., "A DNA sequencing strategy that requires only five bases of known terminal sequence for priming," *Proc. Natl. Acad. Sci. USA*, 92:10162–10166, Oct., 1995.
Fu et al., "Sequencing double–stranded DNA by strand displacmeent," *Nucl. Acids Res.*, 25(3):677–679, Feb., 1997.
Makarov et al., "Long G tails at both ends of human chromosomes suggest a C strand degradation mechanism for telomere shortening," *Cell*, 88:657–666, Mar. 7, 1997.
Wellinger et al., "Evidence for a new step in telomere maintainance," *Cell*, 85:423–433, 1996.
Wellinger et al., "Origin activation and formation of single strand $TG_{1-3}$ tails occur sequentially in late S phase on a yeast linear plasmid," *Mol. Cell. Biol.*, 13:4057–4065, 1993.
Wellinger et al., "Sacharomyces telomeres aquire single–strand $TG_{1-3}$ tails late in S phase," *Cell*, 72:51–60, 1993.
Wellinger et al., "Use of non–denaturing Southern hybridization and two dimensional agarose gels to detect putative intermediates in telomere replication in *Sacharomyces cerevisae*," *Chromosoma*, 102, S150–S156, 1992.
Chiu et al., "Differential dependence on chromatin structure for copper and iron induction of DNA double–strand breaks," *Biochemistry* 34:2653–2661, 1995.
Dear and Cook, "Happy mapping: linkage mapping using a physical analogue of meiosis," *Nucl. Acids Res.* 21:13–20, 1993.
Fitzgerald et al., "Rapid shotgun cloning utilizing the two base recognition endonocluease CviJI," *Nucl. Acids Res.* 20:3753–3762, 1992.
Gish and Eckstein, "DNA and RNA sequence determination based on phosphorothioate chemistry," *Science* 240: 1520–1522, 1988.
Grecz et al., "Freeze–thaw injury: evidence for double–stand breaks in *Escherichia coli* DNA," *Biochem. Biophys. Res. Comm.* 93:1110–1113, 1980 (Medicine abstract).
Matsugo et al., "DNA strand scission and cell–killing activity of hydroperoxynaphthalimide derivatives upon photoirradiation," *Nucl. Acids Symp. Ser.* 25:109–110, 1991 (HCA abstract).
International Search Report dated Jan. 12, 1999 (PCT/US98/ 04423) (UMIC:027P).

(List continued on next page.)

*Primary Examiner*—Eggerton A. Campbell
*Attorney, Agent, or Firm*—Fulbright & Jaworski

[57] ABSTRACT

An improvement over the standard Sanger Method for nucleic acid sequencing is described. The novel method does not require denaturation of double-stranded template; rather, sequencing can be carried out directly on the double-stranded template. Embodiments are described with and without oligonucleotide primers.

21 Claims, 19 Drawing Sheets-

OTHER PUBLICATIONS

Lindahl, "DNA Glycosylases, Endonucleases for Apurinic/Apyrimidinic Sites, and Base Excision–Repair," *Prog. Nucleic Acid Res. Mol. Biol.* 22:135–192, 1979.

Partial International Search Report dated Aug. 17, 1998 (PCT/US98/04423)(UMIC:027P).

Ehrlich, et al. "The specificity of pancreatic deoxyribonuclease," *Eur J Biochem.* 40:143–147, 1973.

Kovacs et al., "The generation of a single nick per plasmid molecule using restriction endonucleases with multiple recognition sites," *Gene*, 29:63, 1984.

Meyer and Geider, "Bacteriophage fd gene II–protein. I. Purification, involvement in RF replication, and the expression of gene II," *J. Biol. Chem.*, 254:12636, 1979.

Olsen et al., "Investigation of the inhibitory role of phosphorothioate internucleotidic linkages on the catalytic activity of the restriction endonuclease EcoRV," *Biochem.*, 29:9546, 1990.

Co–pending U.S. application No. 09/035,677 filed Mar. 5, 1998 (UMIC:027).

Labeit et al., "Laboratory methods: A new method of DNA sequencing using deoxynucleotide α–thiotriphosphates," *DNA*, 5(2):173–177, 1986.

Porter et al., "Direct PCR sequencing with boronated nucleotides," *Nucl. Acids Res.*, 25(8):1611–1617, 1997.

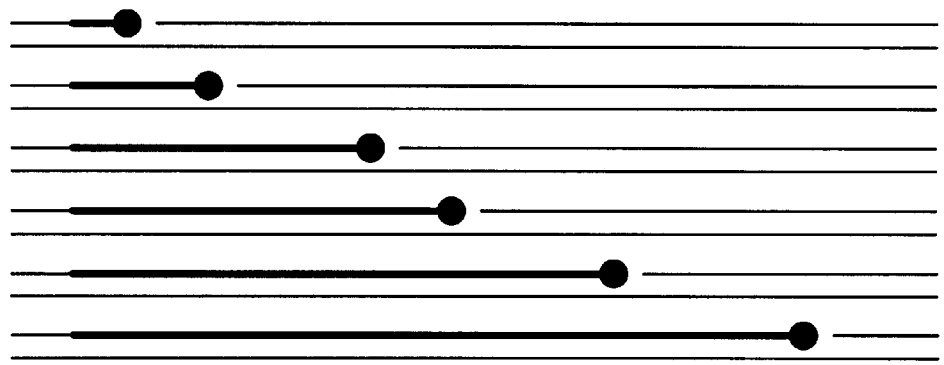
FIG. 4F
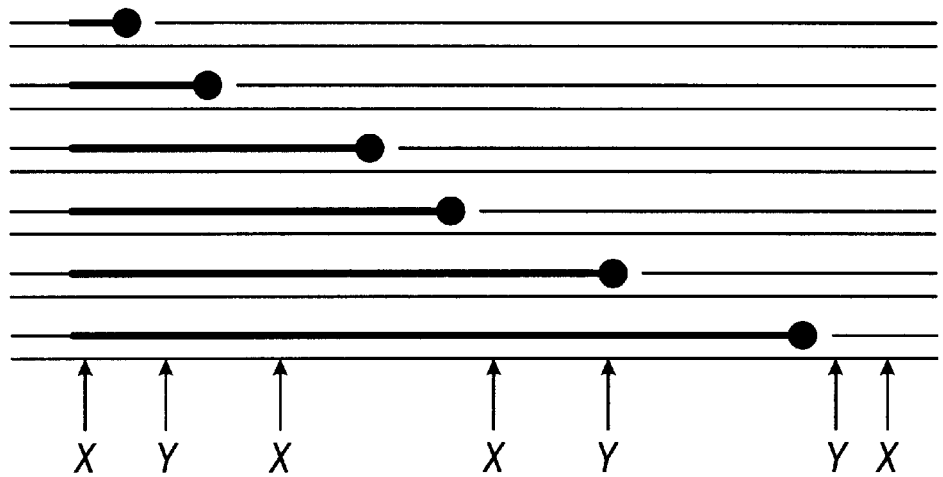
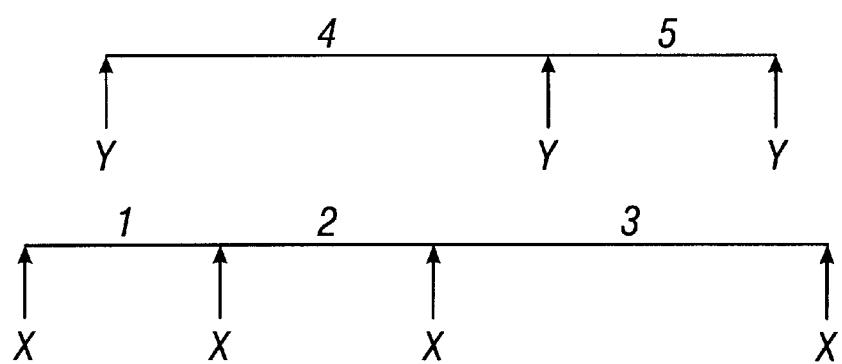
FIG. 4G

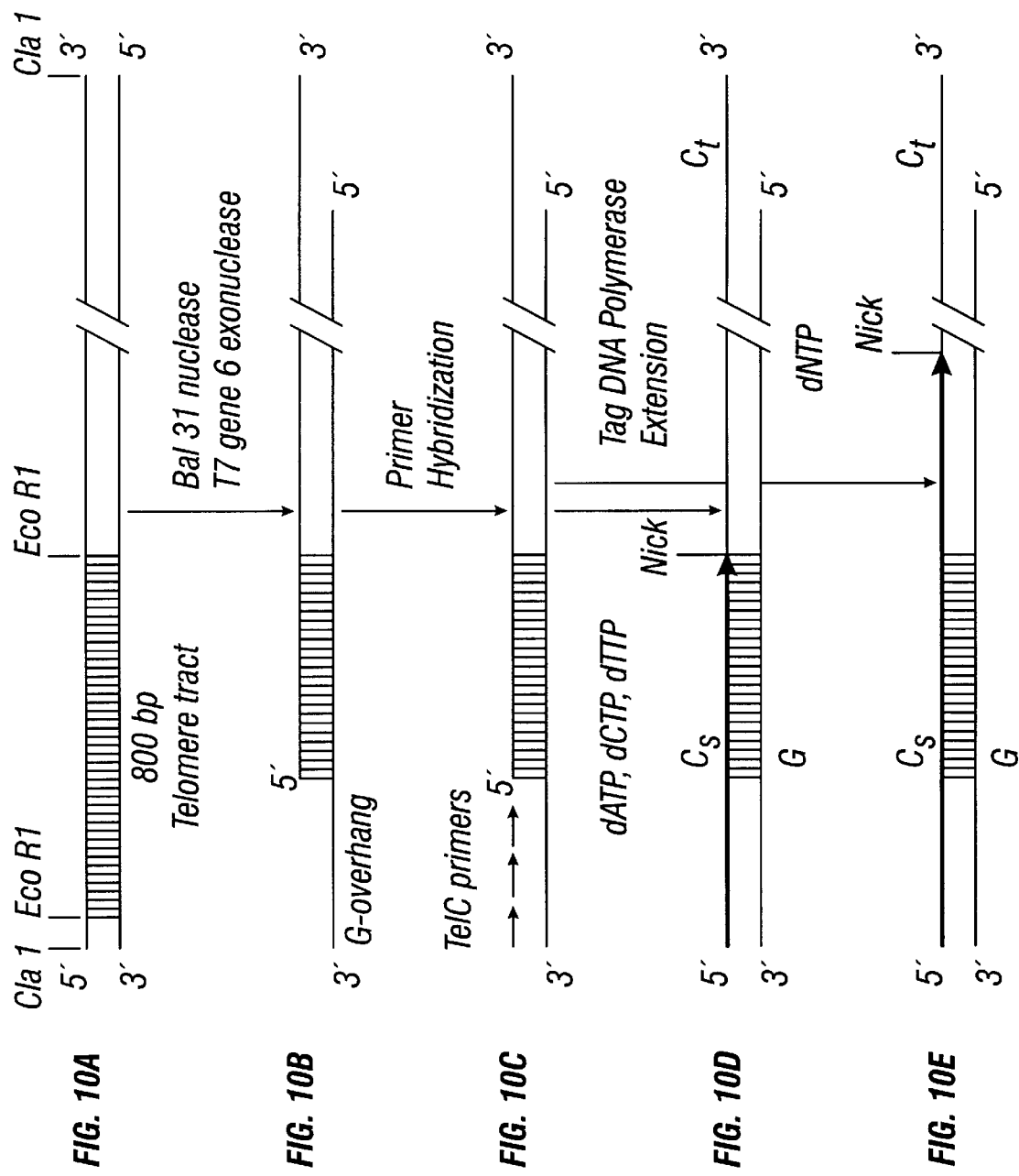

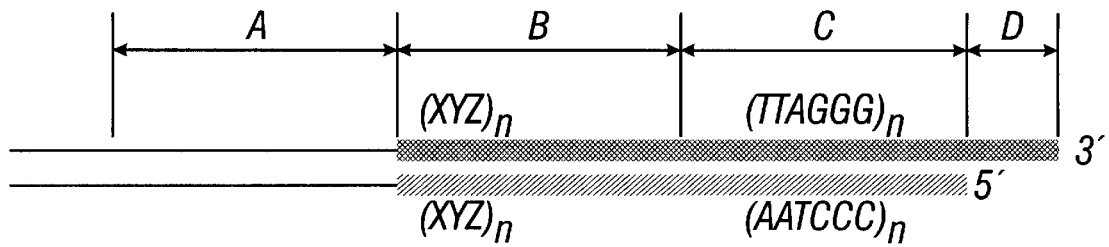
reaction time (min)
with dUTP    with dTTP
0            1
10           1
20           1
30           1
40           1
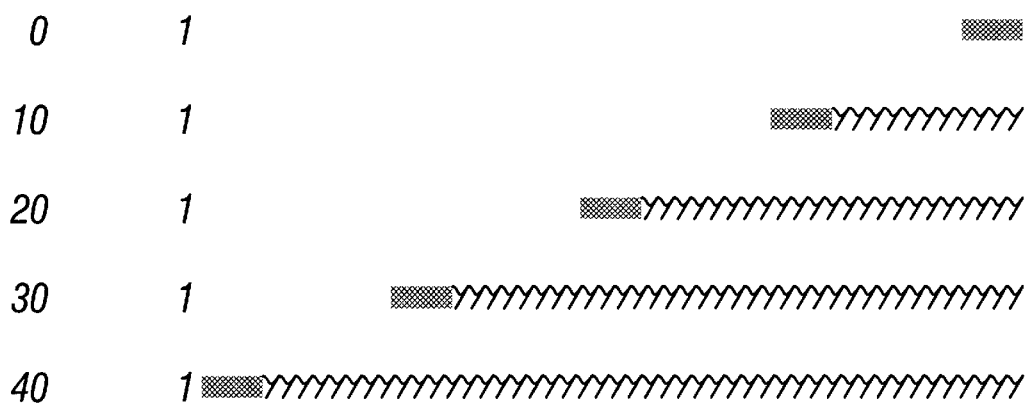
▓▓▓ = thymidine-containing DNA synthesized by SR
ууу = uridine-containing DNA synthesized by SR
FIG. 16

NUCLEIC ACID SEQUENCING AND MAPPING

This invention was made with government support awarded by the National Science Foundation. The government has certain rights in the invention.

FIELD OF THE INVENTION

The invention relates to nucleic acid sequencing and mapping and, more particularly, to the sequencing and mapping of double-stranded nucleic acid templates.

BACKGROUND

An aggressive research effort to sequence the entire human genome is proceeding in the laboratories of genetic researchers throughout the country. The project is called the Human Genome Project (HGP). It is a daunting task given that it involves the complete characterization of the archetypal human genome sequence which comprises $3 \times 10^9$ DNA nucleotide base pairs. Early estimates for completing the task within fifteen years hinged on the expectation that new technology would be developed in response to the pressing need for faster methods of DNA sequencing.

Current approaches generally incorporate the fundamentals of either the Sanger sequencing method or the Maxam and Gilbert sequencing method, two techniques that were first introduced in the 1970's. [Sanger et al, (1977) "DNA Sequencing with Chain-Terminator Inhibitors," Proc. Natl. Acad. Sci. USA 74:5463–5467); Maxam and Gilbert, (1977) "A new method for sequencing DNA," Proc. Natl. Acad. Sci. USA, 74:560–564]. In the Sanger Method, a short oligonucleotide or primer is annealed to a single-stranded template containing the DNA to be sequenced. The primer provides a 3' hydroxyl group which allows the polymerization of a chain of DNA when a polymerase enzyme and dNTPs are provided. The Sanger method is an enzymatic reaction that utilizes chain-terminating dideoxynucleotides (ddNTPs). ddNTPs are chain-terminating because they lack a 3'-hydroxyl residue which prevents formation of a phosphodiester bond with a succeeding deoxyribonucleotide (dNTP). A small amount of one ddNTP is included with the four conventional dNTPs in a polymerization reaction. Polymerization or DNA synthesis is catalyzed by a DNA polymerase. There is competition between extension of the chain by incorporation of the conventional dNTPs and termination of the chain by incorporation of a ddNTP.

The original version of the Sanger method utilized the E. coli DNA polymerase I ("pol I"), which has a polymerization activity, a 3'-5' exonuclease proofreading activity, and a 5'-3' exonuclease activity. Later, an improvement to the method was made by using Klenow fragment instead of pol I; Klenow lacks the 5'-3' exonuclease activity that is detrimental to the sequencing reaction because it leads to partial degradation of template and product DNA. The Klenow fragment has several limitations when used for enzymatic sequencing. One limitation is the low processivity of the enzyme, which generates a high background of fragments that terminate by the random dissociation of the enzyme from the template rather than by the desired termination due to incorporation of a ddNTP. The low processivity also means that the enzyme cannot be used to sequence nucleotides that appear more than ~250 nucleotides from the 5' end of the primer. A second limitation is that Klenow cannot efficiently utilize templates which have homopolymer tracts or regions of high secondary structure. The problems caused by secondary structure in the template can be reduced by running the polymerization reaction at 55° C. (R. Gomer and R. Firtel, "Sequencing homopolymer regions." Bethesda Res. Lab. Focus 7:6 1985).

Improvements to the original Sanger method include the use of polymerases other than the Klenow fragment. Reverse transcriptase has been used to sequence templates that have homopolymeric tracts (S. Karanthanasis, "M13 DNA sequencing using reverse transcriptase" Bethesda Res. Lab. Focus 4(3):6 1982; Graham et al, "Direct DNA sequencing using avian myeloblastosis virus and Moleney murine leukemia virus reverse transcriptase" Bethesda Res. Lab. Focus 8(2):4 1986). Reverse transcriptase is somewhat better than the Klenow enzyme at utilizing templates containing homopolymer tracts.

The use of a modified T7 DNA polymerase (Sequenase™) was a significant improvement to the Sanger method. See Sambrook, J. et al. Molecular Cloning, A Laboratory Manual, 2d Ed. Cold Spring Harbor Laboratory Press, New York, 13.7– 13.9 and Hunkapiller, M. W. (1991) Curr. Op. Gen. Devl. 1:88–92. T7 DNA polymerase does not have any inherent 5'-3' exonuclease activity and has a reduced selectivity against incorporation of ddNTP. However, the 3'-5' exonuclease activity leads to degradation of some of the oligonucleotide primers. Sequenase™ is a chemically-modified T7 DNA polymerase that has reduced 3' to 5' exonuclease activity (Tabor et al. 1987, Proc. Natl. Acad. Sci. USA 84:4767). Sequenase™ version 2.0 is a genetically engineered form of the T7 polymerase which completely lacks 3' to 5' exonuclease activity. Sequenase™ has a very high processivity and high rate of polymerization. It can efficiently incorporate nucleotide analogs such as dITP and 7-deaza-dGTP which are used to resolve regions of compression in sequencing gels. In regions of DNA containing a high G+C content, Hoogsteen bond formation can occur which leads to compressions in the DNA. These compressions result in aberrant migration patterns of oligonucleotide strands on sequencing gels. Because these base analogs pair weakly with conventional nucleotides, intrastrand secondary structures during electrophoresis are alleviated. In contrast, Klenow does not incorporate these analogs as efficiently.

The use of Taq DNA polymerase and mutants thereof is a more recent addition to the improvements of the Sanger method [see U.S. Pat. No. 5,075,216 to Innis et al. (1993), hereby incorporated by reference]. Taq polymerase is a thermostable enzyme which works efficiently at 70–75° C. The ability to catalyze DNA synthesis at elevated temperature makes Taq polymerase useful for sequencing templates which have extensive secondary structures at 37° C. (the standard temperature used for Klenow and Sequenase™ reactions). Taq polymerase, like Sequenase™, has a high degree of processivity and like Sequenase 2.0, it lacks 3' to 5' nuclease activity. The thermal stability of Taq and related enzymes (such as Tth and Thermosequenase™) provides an advantage over T7 polymerase (and all mutants thereof) in that these thermally stable enzymes can be used for cycle sequencing which amplifies the DNA during the sequencing reaction, thus allowing sequencing to be performed on smaller amounts of DNA. Optimization of the use of Taq in the standard Sanger Method has focused on modifying Taq to eliminate the intrinsic 5'-3' exonuclease activity and to increase its ability to incorporate ddNTPs to reduce incorrect termination due to secondary structure in the single-stranded template DNA. Tabor and Richardson, EP 0 655 506 B1, hereby incorporated by reference.

Both the Sanger and the Maxim/Gilbert methods produce populations of radiolabelled or fluorescently labeled polynucleotides of differing lengths which are separated according to size by polyacrylamide gel electrophoresis (PAGE). The nucleotide sequence is determined by analyzing the pattern of size-separated radiolabelled polynucleotides in the gel.

The current limitations to conventional applications of the Sanger Method include 1) the limited resolving power of polyacrylamide gel electrophoresis, 2) the formation of intermolecular and intramolecular secondary structure of the denatured template in the reaction mixture, which can cause any of the polymerases to prematurely terminate synthesis at specific sites or misincorporate ddNTPs at inappropriate sites, 3) secondary structure of the DNA on the sequencing gels can give rise to compressions of the electrophoretic ladder at specific locations in the sequence, 4) cleavage of the template, primers and products with the 5'-3' or 3'-5' exonuclease activities in the polymerases, and 5) mispriming of synthesis due to hybridization of the oligonucleotide primers to multiple sites on the denatured template DNA. The formation of intermolecular and intramolecular secondary structure produces artificial terminations that are incorrectly "read" as the wrong base, gives rise to bands across four lanes (BAFLs) that produce ambiguities in base reading, and decrease the intensity and thus signal-to-noise ratio of the bands. Secondary structure of the DNA on the gels can largely be solved by incorporation of dITP or 7-deaza-dGTP into the synthesized DNA; DNA containing such modified NTPs is less likely to form urea-resistant secondary structure during electrophoresis. Cleavage of the template, primers or products leads to reduction in intensity of bands terminating at the correct positions and increase the background. Mispriming gives rise to background in the gel lanes.

The net result is that, although the inherent resolution of polyacrylamide gel electrophoresis alone is as much as 1000 nucleotides, it is common to only be able to correctly read 400–600 nucleotides of a sequence (and sometimes much less) using the conventional Sanger Method, even when using optimized polymerase design and reaction conditions. Some sequences such as repetitive DNA, strings of identical bases (especially guanines, GC-rich sequences and many unique sequences) cannot be sequenced without a high degree of error and uncertainty.

In the absence of any methods to sequence DNA longer than 400–800 bases, investigators must subclone the DNA into small fragments and sequence these small fragments. The procedures for doing this in a logical way are very labor intensive, cannot be automated, and are therefore impractical. The most popular technique for large-scale sequencing, the "shotgun" method, involves cloning and sequencing of hundreds or thousands of overlapping DNA fragments. Many of these methods are automated, but require sequencing 5–10 times as many bases as minimally necessary, leave gaps in the sequence information that must be filled in manually, and have difficulty determining sequences with repetitive DNA.

Thus, the goal of placing rapid sequencing techniques in the hands of many researchers is yet to be achieved. New approaches are needed that eliminate the above-described limitations.

SUMMARY OF THE INVENTION

The invention relates to nucleic acid sequencing and mapping and, more particularly, to the sequencing and mapping of double-stranded nucleic acid templates. The invention employs a suitable polymerase to synthesize a new DNA strand using an undenatured, double-stranded DNA. This strand replacement (SR) reaction involves no net synthesis of DNA; elongation of the synthetic reaction requires the stepwise removal of one strand of the template at or within a few nucleotides of the site of synthesis so that the DNA remains almost completely double-stranded at every moment during the reaction.

The unique aspects of the method of the present invention include 1) use of polymerases optimized to possess strong 5'-3' exonuclease activity, 2) use of a double-stranded, undenatured DNA template, 3) the ability to optimize the reaction conditions using lower temperature, higher salt, and other conditions designed to stabilize native Watson-Crick secondary structure in the template, 4) initiation of a sequencing reaction with a nick or gap of a double-stranded template, including the use of novel double-stranded adapters specifically designed to create unique strand replacement initiation sites when ligated to the end of restriction fragments, 5) elongation in a manner that the DNA remains double-stranded, and 6) termination of synthesis at either a ddNTP or other site-specific location.

Because the sequencing method of the present invention begins and continues with double-stranded DNA, the method avoids the formation of intermolecular and intramolecular secondary structure of the template in the reaction mixture. Moreover, the present invention contemplates embodiments where no primer is necessary; in this embodiment (Primer Independent Strand Replacement), there is no concern of cleavage of the primers or mispriming, and the initiation of the sequencing reaction is highly efficient and specific.

While the SR technique of the present invention is carried out without a denaturation step to generate single-stranded template, the method can (if desired) also be used with a primer and a double-stranded template with a short single-stranded region. This Primer Dependent Strand Replacement can be used with double-stranded templates having 1) naturally-occurring single-stranded regions (such as the 3' overhangs of double-stranded telomeric DNA), 2) synthetically- or enzymatically-introduced single-stranded regions, or 3) regions created by ligation to special oligonucleotide adapters.

The product molecules are double-stranded, allowing for long stretches of the product DNA to be subsequently cleaved (using restriction enzymes) into smaller fragments for direct sequencing and other forms of analysis using conventional acrylamide or agarose gel electrophoresis. The sequencing of these restriction fragments allows for much longer DNA fragments to be sequenced without the need for subcloning. For sequencing purposes, the newly-synthesized strands are terminated at base-specific locations using either ddNTPs or other base-specific termination nucleotides and can be subjected to automated sequencing in commercially available sequenators.

Although the method is contemplated to find extensive application to determining the base sequence of DNA, the same principles can be applied to the mapping of sequences and sequence variations at lower resolution over long distances.

In one embodiment, the present invention contemplates sequencing of DNA to one side (e.g., clockwise) from a restriction site in a circular molecule of DNA. This method depends upon a reliable, specific method for introducing a nick in one specific strand. In another embodiment, both sides of a single internal restriction site (clockwise and counterclockwise) are sequenced in a covalently-closed circular or linear DNA molecule.

In one embodiment, the present invention contemplates a method for sequencing nucleic acid, comprising: a) providing: i) nucleic acid template capable of being double-stranded, ii) a polymerase having a polymerase activity and a 5'-3' exonuclease activity, iv) a nucleic acid precursor, and iii) a terminating agent; b) mixing said polymerase, said precursors, said terminating agents and said template to create a reaction under conditions where said template is substantially double-stranded; and c) detecting product of said reaction under conditions whereby the nucleic acid sequence of at least a portion of said template is revealed. In one embodiment said template capable of being double-stranded comprises single-stranded nucleic acid that, upon cooling becomes substantially double-stranded.

In another embodiment, the present invention contemplates a method for sequencing nucleic acid, comprising: a) providing: i) substantially double-stranded nucleic acid template, ii) a polymerase having synthetic activity and a 5'-3' exonuclease activity, iii) at least one nucleic acid precursors, and iv) at least one terminating agent; b) mixing said polymerase, said precursor, said terminating agent and said template under conditions such that nucleic acid synthesis takes place for a reaction period during which said template remains substantially double-stranded and nucleic acid product is created containing said terminating agent; and c) detecting said product of said reaction under conditions whereby the nucleic acid sequence of at least a portion of said template is revealed.

In yet another embodiment, the present invention contemplates a method for sequencing nucleic acid, comprising: a) providing: i) substantially double-stranded nucleic acid template, ii) a polymerase having synthetic activity and a 5'-3' exonuclease activity, iii) one or more nucleic acid precursors, and iv) one or more terminating agents; b) mixing said polymerase, said one or more precursors, said one or more terminating agents and said template under conditions such that nucleic acid synthesis takes place for a reaction period during which said template remains substantially double-stranded and nucleic acid product is created containing said one or more terminating agents; and c) detecting said product of said reaction under conditions whereby the nucleic acid sequence of at least a portion of said template is revealed.

In one embodiment, said substantially double-stranded template comprises a single-stranded region. In this embodiment, an oligonucleotide primer can be used. For example, a primer can be added to the reaction of step (b); the primer should be capable of hybridizing to said single-stranded region of said substantially double-stranded template.

In another embodiment, an oligonucleotide primer is not used. Instead, prior to step (b) one strand of said substantially double-stranded template is nicked.

It is not intended that the present invention be limited by the nature of the nucleic acid precursors. In one embodiment, said one or more nucleic acid precursors mixed in step (b) are selected from the group consisting of dATP, dGTP, dTTP and dCTP. Similarly, it is not intended that the present invention be limited by the nature of the terminating agents. In one embodiment, said one or more terminating agents mixed in step (b) are selected from the group consisting of ddATP, ddGTP, ddTTP and ddCTP.

A variety of polymerases are suitable for the strand replacement reaction of the present invention. In one embodiment, the polymerase is Taq DNA polymerase. In another, the polymerase is *E. coli* DNA polymerase I.

It is not intended that the present invention be limited by the method by which the products of the reaction are detected and evaluated. In one embodiment, the detecting comprises gel electrophoresis. That is to say, the products are subjected to gel electrophoresis.

In one embodiment, the present invention contemplates a method for sequencing nucleic acid, comprising: a) providing: i) substantially double-stranded nucleic acid template, ii) an endonuclease capable of specifically nicking one of the strands of said double-stranded nucleic acid template, iii) a polymerase having synthetic activity and a 5'-3' exonuclease activity, iv) one or more nucleic acid precursors, and v) one or more terminating agents; b) mixing said substantially double-stranded template with said endonuclease under conditions such that a substantially double-stranded template is produced containing a nick on one strand; c) adding a solution to said nicked template, said solution comprising said polymerase, said one or more precursors, and said one or more terminating agents, whereby said adding is carried out under conditions such that nucleic acid synthesis takes place for a reaction period during which said template remains substantially double-stranded and nucleic acid product is created containing said one or more terminating agents; and d) detecting said product of said reaction under conditions whereby the nucleic acid sequence of at least a portion of said template is revealed.

By "specifically nicking" it is meant that nicking takes place on only one strand and (preferably) at only one site. In one embodiment, the endonuclease capable of such specific nicking is f1 gpII.

As noted above, said one or more nucleic acid precursors mixed in step (b) may be selected from the group consisting of DATP, dGTP, dTTP and dCTP. In some cases, said one or more nucleic acid precursors are labeled. It is not intended that the present invention be limited by the nature of the label. In one embodiment, the label is selected from the group consisting of radiolabels and fluorescent labels. In a particular case, the label is $^{32}$P. Where the label is a radiolabel, it is desirable that the detecting comprise gel electrophoresis and autoradiography.

As noted above, said one or more terminating agents mixed in step (b) may be selected from the group consisting of ddATP, ddGTP, ddTTP and ddCTP. Such agents can also be labeled.

In a preferred embodiment, the present invention contemplates a method for sequencing nucleic acid, comprising: a) providing: i) substantially double-stranded nucleic acid template, said substantially double-stranded template comprising a single-stranded region, ii) a polymerase having synthetic activity and a 5'-3' exonuclease activity, iii) one or more nucleic acid precursors, iv) one or more terminating agents, and v) a primer capable of hybridizing to said single-stranded region of said substantially double-stranded template; b) mixing said polymerase, said one or more precursors, said one or more terminating agents, said primer and said template under conditions such that nucleic acid synthesis takes place for a reaction period during which said template remains substantially double-stranded and nucleic acid product is created containing said one or more terminating agents; and c) detecting said product of said reaction under conditions whereby the nucleic acid sequence of at least a portion of said template is revealed. In one embodiment, such template is telomeric DNA, including but not limited to human telomeric DNA having 3' overhangs. In one embodiment, the primer used to hybridize to said telomeric DNA comprises the sequence CCCUAA, including but not limited to a primer having the sequence (CCCUAA)$_4$.

The present invention also contemplates special adapters useful in conjunction with the strand replacement method of the present invention. Such adapters are ligated to create an initiation site for strand replacement.

DEFINITIONS

As used herein, the term "amplifiable nucleic acid" is used in reference to nucleic acids which may be amplified by any amplification method, including but not limited to PCR.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to fluorescent, enzyme (e.g, ELISA, as well as enzyme-based histochemical assays), radioactive, and luminescent systems. It is not intended that the present invention be limited to any particular detection system or label.

As used herein, the term "template," refers to nucleic acid that is to acted upon, such as nucleic acid that is to be mixed with polymerase. In some cases "template" is sought to be sorted out from other nucleic acid sequences. "Substantially single-stranded template" is nucleic acid that is either completely single-stranded (having no double-stranded areas) or single-stranded except for a proportionately small area of double-stranded nucleic acid (such as the area defined by a hybridized primer or the area defined by intramolecular bonding). "Substantially double-stranded template" is nucleic acid that is either completely double-stranded (having no single-stranded region) or double-stranded except for a proportionately small area of single-stranded nucleic acid (such as the area defined at the ends of telomeric DNA).

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a template sequence in a mixture of genomic DNA without cloning or purification. This process for amplifying the template sequence consists of introducing a large excess of two oligonucleotide primers to the DNA mixture containing the desired template sequence, followed by a precise sequence of thermal cycling in the presence of a DNA polymerase. The two primers are complementary to their respective strands of the double stranded template sequence. To effect amplification, the mixture is denatured and the primers then annealed to their complementary sequences within the template molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired template sequence. The length of the amplified segment of the desired template sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the template sequence become the predominant sequences (in terms of concentration) in the mixture, they are said to be "PCR amplified".

With PCR, it is possible to amplify a single copy of a specific template sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the terms "PCR product", "PCR fragment" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region However, enhancer elements can exert their effect even when located 3' of the promoter element and the coding region. Transcription termination and polyadenylation signals are located 3' or downstream of the coding region.

As used herein, the term "vector" is used in reference to nucleic acid molecules that transfer DNA segment(s) from one cell to another. Vectors are used to introduce foreign DNA into host cells where it can be replicated (i.e., reproduced) in large quantities. The term "vehicle" is sometimes used interchangeably with "vector." Vectors, including "cloning vectors" allow the insertion of DNA fragments without the loss of the vector's capacity for self-replication. Cloning vectors may be derived from viruses, plasmids or genetic elements from eucaryotic and/or procaryotic organisms; vectors frequently comprise DNA segments from several sources. Examples of cloning vectors include plasmids, cosmids, lambda phage vectors, P1 vectors, yeast artificial chromosomes (YACs), and bacterial artificial chromosomes (BACs).

The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. The oligonucleotide may be generated in any manner, including chemical synthesis, DNA replication, reverse transcription, or a combination thereof.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology. Nonetheless, a number of problems have prevented the wide scale use of hybridization as a tool in human diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

The "complement" of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated. The equation for calculating the $T_m$ of nucleic acids is well known in the art. As indicated by standard references, an estimate of the $T_m$ value may be calculated by the equation:

$$T_m = 81.5° C. + 16.6 \log M + 0.41(\% \text{ GC}) - 0.61(\% \text{ form}) - 500/L$$

where M is the molarity of monovalent cations, %GC is the percentage of guanosine and cytosine nucleotides in the DNA, %form is the percentage of formamide in the hybridization solution, and L=length of the hybrid in base pairs [see e.g., Guide to Molecular Cloning Techniques, Ed. S. L. Berger and A. R. Kimmel, in Methods in Enzymology Vol. 152, 401 (1987)]. Other references include more sophisticated computations which take structural as well as sequence characteristics into account for the calculation of $T_m$.

DESCRIPTION OF THE FIGURES

FIGS. 4A through 4I schematically shows one embodiment of the strand replacement method of the present invention used to map the positions of bases along DNA of multiple restriction fragments.

FIGS. 10A through 10E schematically shows the introduction of single-stranded regions in a model telomere double-stranded construct.

(Scanned images)

(Scanned images)

(Scanned images)

FIG. 16 schematically sets forth one embodiment of the strand replacement method for measuring different distances from the termini of chromosomes.

DESCRIPTION OF THE INVENTION

Figure 1:
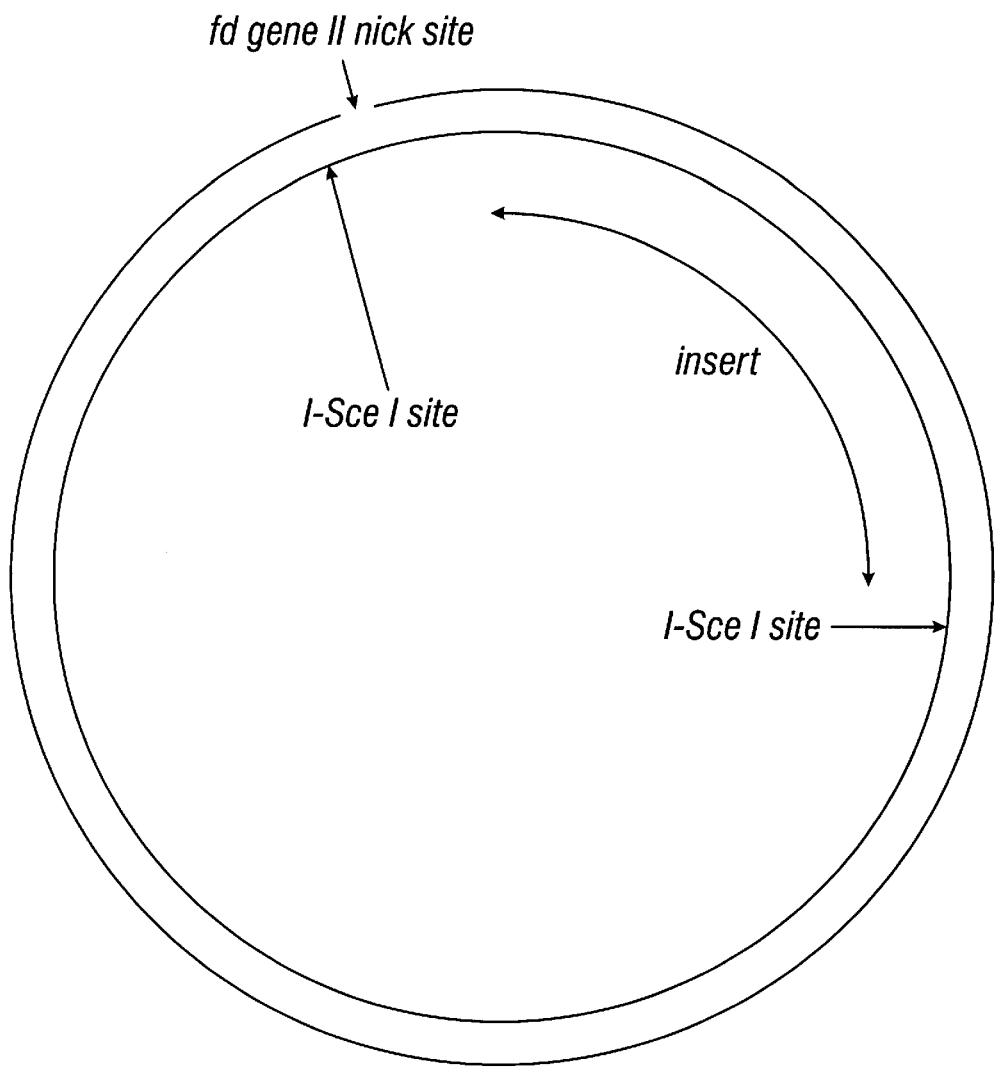
FIG. 1 schematically shows one embodiment of the method of double-stranded sequencing of the present invention utilizing a unique vector.

The invention can be considered to be an improvement over the standard Sanger Method. As noted above, the Sanger enzymatic method (i.e., dideoxy chain termination method) requires a DNA polymerase enzyme to elongate a short primer DNA that is hybridized to a single-stranded template. In other words, current Sanger DNA sequencing protocols require that double-stranded DNA for sequencing first be denatured to enable the primer to bind to the priming site. See generally G. Murphy, In: Methods in Molecular Biology (1993). By contrast, the present invention does not contemplate denaturation of the double-stranded template; rather, sequencing can be carried out directly on the double-stranded template.

The Description of the Invention addresses: A) Conventional Sanger Sequencing, B) Sequencing Using Strand Replacement, C) Microsequencing and D) Application to Mapping of Telomeric DNA.

A) Conventional Sanger Sequencing

The Sanger technique involves 1) denaturation to generate single-stranded DNA, 2) hybridization of an oligonucleotide primer to a unique site of known sequence on the single-stranded DNA, 3) extension of the primer using Taq, T7, or other DNA polymerase to generate a double-stranded product, 4) termination of the synthesis at specific bases by using terminating agents [e.g., incorporating specific dideoxyribonucleotides (ddNTPs)], 5) denaturation of the double-stranded product, and 6) electrophoresis of the denatured DNA to separate the molecules by size. If synthesis is performed with all four dNTPs (nucleic acid precursors) and terminated with labeled ddATP then the strands synthesized will all begin with 5' end of the primer and end at different positions where dideoxyriboadenosine has been incorporated in place of adenosine. In this case the distribution of fragment lengths reflect the spatial distribution of thymidine along the template strand. To determine the positions of each of the other three bases, separate reactions can be done to incorporate ddTTP, ddCTP, and ddGTP. For detection the synthetic DNA can be detected by hybridization, incorporation of labeled primers, incorporation of labeled nucleotides, or incorporation of labeled dideoxyribonucleotides. When fluorescently tagged dideoxyribonucleotides with different fluorescent spectra are used to terminate synthesis a laser can be used to distinguish between DNA molecules terminated with each of the four ddNTPs, such that only a single primer extension reaction and single electrophoresis lane needs to be run to determine the position of all four bases.

An important disadvantage of the current Sanger method is that certain sequences (such as strings of guanine) are difficult to sequence due to the propensity of some sequences to form intramolecular and intermolecular secondary structure, which causes the polymerase to terminate prematurely or to add an incorrect dideoxyribonucleotide. In addition each sequencing reaction is only able to determine the sequence of only 400–800 nucleotides immediately adjacent to the primer. The present invention provides a method for overcoming both problems.

B) Sequencing Using Strand Replacement

The method of the present invention represents an enhancement of the Sanger Method. Using a suitable polymerase (described in more detail below), the present invention allows for the sequencing of undenatured, double-stranded DNA. In one embodiment, the process involves a controlled "nicking" of one strand of the double-stranded template followed by a strand replacement (SR).

Template DNA can be any double-stranded DNA molecule including, but not limited to native DNA from any organism, DNA cloned into a bacterial plasmid or virus, PCR products, and artificially synthesized DNA. Linear and circular DNA of all double-stranded conformations isolated by any technique and of any purity can be used. Although it is a requirement that the template DNA be essentially free from nicks or gaps, DNA samples that do not originally meet this requirement can be treated to remove such defects. Nicks in DNA occur after long-term storage or repeated cycles of freezing and thawing; these defects can be repaired by incubating the DNA with a DNA ligase such as that from bacteria phage T4. Gaps can be repaired by incubation with T4 DNA polymerase and ligase.

The fact that the template DNA molecules are double-stranded obviates the problems with unusual secondary structures. Moreover, the fact that the product molecules are double-stranded allows long stretches of the product DNA to be subsequently cleaved using restriction enzymes into fragments sufficiently small that they can be subjected to automated sequencing in commercially available sequenators (e.g. those made by ABI, Pharmicia, and other companies).

Suitable Polymerases

Suitable polymerases are those DNA polymerases that demonstrate a relatively rapid rate of synthesis and have a 5'-3' exonuclease activity to degrade one of the template strands. Examples of preferred polymerases known to have these properties include, but are not limited to E. coli DNA polymerase I [Kornberg and Baker, DNA Replication, Freeman and Co., NY (1992)], DNA polymerase from *Thermus aquaticus* (hereinafter "Taq DNA polymerase"), which is a thermostable enzyme having 5'-3' exonuclease activity but no detectable 3'-5' activity [see Longley, M. J. et al., Nucl. Acids Res. 18:7317 (1990); Holland, P. M., et al., Proc. Natl. Acad. Sci. USA 88:7276 (1991)], pol A from *S. pneumoniae* [Lopez et al., "Characterization of the polA gene of *Streptococcus pneumoniae* and comparison of the DNA polymerase I it encodes to homologous enzymes from *Escherichia coli* and phage T7" J. Biol. Chem. 264:4255 (1989)], Tfl DNA polymerase from *Thermus flavus* [Akhmetzjanov and Vakhitov, "Molecular cloning and nucleotide sequence of the DNA polymerase gene from *Thermus flavus,*" Nucleic Acids Res. 20:5839 (1992)], pol I from *D. radiodurans* [Gutman et al., "Identification, sequencing, and targeted mutagenesis of a DNA polymerase gene required for the extreme radioresistance of *Deinococcus radiodurans,*" J. Bacteriol. 175:3581 (1993)], Tth from *Thermus thermophilus* [Myers and Gelfand, "Reverse transcription and DNA amplification by a *Thermus thermophilus* DNA polymerase," Biochemistry 30:7661 (1991)], recombinant Tth XL from *Thermus thermophilus* (commercially available from Perkin-Elmer), pol I from *M. tuberculosis* [Hiriyanna and Ramakrishnan, "Purification and properties of DNA polymerase from *Mycobacterium tuberculosis* H37Rv," Biochim. Biophys. Acta 652:274 (1981)], pol I from *M. thermoautotrophicum* [Klimczak et al., "Purification and characterization of DNA polymerase from the archaebacterium *Mathanobacterium thermoautotrophicum,*" Biochemistry 25:4850 (1986)], and UL30 from herpes simplex virus [Crute and Lehman, "Herpes simplex-1 DNA polymerase. Identification of an intrinsic 5'-3' exonuclease with ribonuclease H. activity," J. Biol. Chem. 264:19266 (1989)].

In principle, the optimized enzyme could have an associated 3'-5' exonuclease ("proofreading") activity, which might improve the ability to sequence very large molecules of DNA. All of the enzymes listed above (except Taq DNA polymerase, Tth and Tfl) seem to have this proof reading activity.

Optimization of the polymerase used for SR involves testing different polymerases and mutants thereof under the conditions of the sequencing reactions. Indeed, rate of synthesis, fidelity of incorporation of natural and termination nucleotides, and length of the synthesized strands can be adjusted using standard methods (e.g. changing salt conditions, nucleotide triphosphate compositions and concentrations, temperature, time, etc.) known to those familiar with the art of sequencing. Directed mutagenesis of the polymerase is also well-known in the art. Such genetically engineered enzymes can be endowed with both the ability to tolerate a wider range of reaction conditions and improved sequencing product yield.

With regard to genetically engineered enzymes, the present invention specifically contemplates polymerases modified according to the teachings of Tabor and Richardson, EP 0 655 506 B1, hereby incorporated by reference. Such modifications comprise mutations to the binding site which results in better incorporation of dideoxy-nucleotides (as compared to unmodified polymerases), while retaining a strong 5'-3' exonuclease activity.

Initiation of Strand Replacement

The initiation site (as distinct from an oligonucleotide primer) can be introduced by any method that results in a free 3' OH group on one side of a nick or gap in otherwise double-stranded DNA, including, but not limited to such groups introduced by a) digestion by a restriction enzyme under conditions that only one strand of the double-stranded DNA template is hydrolyzed, b) random nicking by a chemical agent or an endonuclease such as DNAase I, c) nicking by f1 gene product II or homologous enzymes from other filamentous bacteriophage [Meyer and Geider, "Bacteriophage fd gene II-protein. I. Purification, involvement in RF replication, and the expression of gene II," J. Biol. Chem. 254:12636 (1979)], or d) chemical nicking of the template directed by triple-helix formation [see Grant and Dervan, "Sequence-specific alkylation and cleavage of DNA mediated by purine motif triple helix formation," Biochemistry 35:12313 (1996)].

Initiation can also be accomplished with an oligonucleotide primer. Such methods include, but are not limited to 1) introduction of one or more oligonucleotide primers at the end or within the template DNA by local disruption of the DNA helix, and 2) introduction of one or more oligonucleotide primers at the end or within the template DNA by removal of a few bases from one strand (e.g. by digestion of the end of DNA by T7 gene 6 exonuclease).

Ligation can also be used to create an initiation site. This very powerful and general method to introduce an initiation site for strand replacement synthesis employs a panel of special double-stranded oligonucleotide adapters designed specifically to be ligated to the termini produced by restriction enzymes. Each of these adapters is designed such that the 3' end of the restriction fragment to be sequenced can be covalently joined (ligated) to the adaptor, but the 5' end cannot. Thus the 3' end of the adaptor remains as a free 3' OH at a 1 nucleotide gap in the DNA, which can serve as an initiation site for the strand-replacement sequencing of the restriction fragment. Because the number of different 3' and 5' overhanging sequences that can be produced by all restriction enzymes is finite, and the design of each adaptor will follow the same simple strategy, above, the design of every one of the possible adapters can be foreseen, even for restriction enzymes that have not yet been identified. To facilitate sequencing, a set of such adapters for strand replacement initiation can be synthesized with labels (radioactive, fluorescent, or chemical) and incorporated into the dideoxyribonucleotide-terminated strands to facilitate the detection of the bands on sequencing gels.

More specifically, adapters with 5' and 3' extensions can be used in combination with restriction enzymes generating 2-base, 3-base and 4-base (or more) overhangs. The sense strand (the upper strand shown in Table 1 below) of the adaptor has a 5' phosphate group that can be efficiently ligated to the restriction fragment to be sequenced. The anti-sense strand (bottom, underlined) is not phosphorylated at the 5' end and is missing one base at the 3' end, effectively preventing ligation between adapters. This gap does not interfere with the covalent joining of the sense strand to the restriction fragment, and leaves a free 3'OH site in the anti-sense strand for initiation of strand replacement synthesis.

TABLE 2

Base Extensions And Restriction Enzymes

| | Restriction endonucleases |
|---|---|
| 2-base extensions | |
| 5'-CG | Mae II, Hin PI, Nar I, Acy I, HpaII, Msp I, Taq I, Cla I, Sfu I, Asu II |
| 5'-GC | ------ |
| 5'-TA | Nde I, Mae I, Mse I, Asn I |
| 5'-AT | Acc I |
| CG-3' | Cfo I, Hha I |
| GC-3' | Ksp I, Sac II |
| TA-3' | ------ |
| AT-3' | Pvu I |
| 3-base extensions | |
| 5'-GNC | Sau 96, Dra II |
| 5'-CNG | ------ |
| 5'-ANT | Hinf I |
| 5'-TNA | Dde I, Cel II, Sau I, Bsu 36 I |
| GNC-3' | Pss I |
| CNG-3' | ------ |
| ANT-3' | ------ |
| TNA-3' | ------ |

TABLE 1

Adapters For Initiation of Strand Replacement DNA Synthesis

```
(a) 2-base 5' restriction extensions:        5'-------
                                             3'-------ab
         Adapters with 3-base 5' extensions:         abcd-------3'
                                                        d-------5'
         Ligation product formed:            5'-------abcd-------3'
                                             3'-------ab d-------5'

(b) 3-base 5' restriction extensions:        5'-------
                                             3'-------abc
         Adapters with 4-base 5' extensions:         abcde-----3'
                                                        e-----5'

(c) 4-base 5' restriction extensions:        5'-------
                                             3'-------abcd
         Adapters with 5-base 5' extensions:         abcdef----3'
                                                        f----5'

(d) 2-base 3' restriction extensions:        5'-------ab
                                             3'-------
         Adapters with 1-base 3' extensions:            c------3'
                                                       bc------5'

(e) 3-base 3' restriction extensions:        5'-------abc
                                             3'-------
         Adapters with 2-base 3' extensions:            d-----3'
                                                      bcd-----5'

(f) 4-base 3' restriction extensions:        5'-------abcd
                                             3'-------
         Adapters with 3-base 3' extensions             e-----3'
                                                     bcde-----5'
```

TABLE 2-continued

Base Extensions And Restriction Enzymes

| | Restriction endonucleases |
|---|---|
| 4-base extensions | |
| 5'-AATT | Eco RI |
| 5'-GATC | Mbo I, Nde II, Sau 3A, Bgl II, Bam HI, Bcl I, Xho II |
| 5'-CATG | Nco I, Bsp HI |
| 5'-TATA | ------ |
| 5'-ATAT | ------ |
| 5'-GTAC | Asp 718, Spl I |
| 5'-CTAG | Spe I, Nhe I, Avr II, Xba I |
| 5'-TTAA | Afl II |
| 5'-AGCT | Hind III |
| 5'-GGCC | Ecl XI, Xma III, Not I, Eae I |
| 5'-CGCG | Mlu I, Bss HII |
| 5'-TGCA | Sno I |
| 5'-ACGT | ------ |
| 5'-GCGC | Ban I |
| 5'-CCGG | Xma I, Mro I, Cfr 101, Sgr Al, Acc III |
| 5'-TCGA | Sal I, Xho I |
| AATT-3' | ------ |
| GATC-3' | ------ |
| CATG-3' | Nla III, Sph I, Nsp I |
| TATA-3' | ------ |
| ATAT-3' | ------ |
| GTAC-3' | Kpn I |
| CTAG-3' | ------ |
| TTAA-3' | ------ |
| AGCT-3' | Sac I |
| GGCC-3' | Apa I |
| CGCG-3' | ------ |
| TGCA-3' | Nsi I, Pst I |
| ACGT-3' | Aat II |
| GCGC-3' | Bbe I, Hae II |
| CCGG-3' | ------ |
| TCGA-3' | ------ |

The adapters can also be designed to have a nick rather than a gap, which will still facilitate initiation of the strand replacement reaction. To do this, the restriction fragments need to be dephosphorylated to prevent ligation of the 5' end. In this case, blunt end adapters that are compatible with blunt end producing restriction enzymes can be used.

Termination

Strand Replacement reactions are terminated by incorporation of a dideoxyribonucleotide instead of the homologous naturally-occurring nucleotide. This terminates growth of the new DNA strand at one of the positions that was formerly occupied by dA, dT, dG, or dC by incorporating ddA, ddT, ddG, or ddC. In principle the reaction can be terminated using any suitable nucleotide analogs that prevent continuation of DNA synthesis at that site. For specific mapping applications, such as the determination of the length of telomeres, the polymerization reaction can be terminated when the polymerase cannot insert a particular nucleotide, because it is missing from the reaction mixture.

Polymerization can also be terminated specific distances from the priming site by inhibiting the polymerase a specific time after initiation. For example, under specific conditions Taq DNA polymerase is capable of strand replacement at the rate of 250 bases/minute, so that arrest of the polymerase after 10 minutes occurs about 2500 bases from the initiation site. This strategy allows for pieces of DNA to be isolated from different locations in the genome.

Cleavage

Because all of the template and synthetic DNA remains double-stranded, except at the site of termination, where there is a nick or small gap, restriction enzymes can be used to cut the DNA at sequence specific sites. At least one hundred of these cleavage reagents are commercially available and are able to make double-strand scissions in the DNA in short times. In addition to these natural sequence specific endonucleases there are a number of chemical reagents developed to make specific breaks in DNA [see Strobel and Dervan, "Triple helix-mediated single-site enzymatic cleavage of megabase genomic DNA," Methods Enzymol. 216:309 (1992); Grant and Dervan, "Sequence-specific alkylation and cleavage of DNA mediated by purine motif triple helix formation," Biochemistry 35:12313 (1996)].

Separation Of Fragments

Separation of sequence-specific double-stranded DNA fragments can be achieved by fractionation according to size using electrophoresis through media, including agarose, polyacrylamide, and polymer solutions. The physical form of the media can include flat layers, tubes and capillaries. Size fractionation can also be achieved by flow of solution through chromatographic media by the techniques of HPLC and FPLC. The ability to fractionate DNA according to length is not affected by the presence of nicks in the double-stranded DNA. For example, it is well-known that nicked double-stranded DNA forms sharp bands during electrophoresis [Higashitani et al., "A single amino acid substitution reduces the superhelicity requirement of a replication initiator protein," Nucleic Acids Res. 30:2685 (1992)]. Preparative collection of the DNA after separation can be performed manually by cutting pieces from gels, allowing the samples to flow into collection vessels, or by automatically sorting liquid samples. Typically, the fractions containing DNA fragments are detected by absorption spectrophotometry, fluorescence, radioactivity, or some other physical property.

In specific cases size fractionation before sequencing gels is not required for sequencing a specific restriction fragment. These cases include those where (a) only one restriction site is present in the DNA to be sequenced, (b) only one restriction fragment is long enough or short enough to give a good sequencing gel, and (c) two restriction fragments are produced, but one is removed from the reaction using an affinity immobilization or separation, e.g., based on the presence of biotin, digoxigenin, or a triplex-forming nucleotide on one of the fragments that leads to immobilization on magnetic beads, surfaces, or matrices, and d) only one restriction fragment is labeled.

C) Microsequencing

The present invention contemplates carrying out the novel sequencing method described above using microscale devices. Thus, sequencing reactions using double-stranded template are contemplated to take place in microfabricated reaction chambers. The present invention contemplates that suitable microscale devices comprise microdroplet transport channels, reaction regions (e.g., chambers), electrophoresis modules, and radiation detectors. In a preferred embodiment, these elements are microfabricated from silicon substrates according to those methods known in the art. As a mechanical building material, silicon has well-known fabrication characteristics. The economic attraction of silicon devices is that their associated micromachining technologies are, essentially, photographic reproduction techniques. In these processes, transparent templates or masks containing opaque designs are used to photodefine objects on the surface of the silicon substrate. The patterns on the templates are generated with computer-aided design programs and can delineate structures with line-widths of less than one micron. Once a template is generated, it can be used almost indefinitely to produce identical replicate structures. Consequently, even extremely complex micromachines can be reproduced in mass quantities and at low incremental unit cost—provided that all of the components are compatible with the silicon micromachining process. While other substrates, such as glass or quartz, can use photolithographic methods to construct microfabricated analysis devices, only silicon gives the added advantage of allowing a large variety of electronic components to be fabricated within the same structure.

The principal modern method for fabricating semiconductor integrated circuits is the so-called planar process. The planar process relies on the unique characteristics of silicon and comprises a complex sequence of manufacturing steps involving deposition, oxidation, photolithography, diffusion and/or ion implantation, and metallization, to fabricate a "layered" integrated circuit device in a silicon substrate. See e.g., W. Miller, U.S. Pat. No. 5,091,328, hereby incorporated by reference.

For example, oxidation of a crystalline silicon substrate results in the formation of a layer of silicon dioxide on the substrate surface. Photolithography can then be used to selectively pattern and etch the silicon dioxide layer to expose a portion of the underlying substrate. These openings in the silicon dioxide layer allow for the introduction ("doping") of ions ("dopant") into defined areas of the underlying silicon. The silicon dioxide acts as a mask; that is, doping only occurs where there are openings. Careful control of the doping process and of the type of dopant allows for the creation of localized areas of different electrical resistivity in the silicon. The particular placement of acceptor ion-doped (positive free hole, "p") regions and donor ion-doped (negative free electron, "n") regions in large part defines the interrelated design of the transistors, resistors, capacitors and other circuit elements on the silicon wafer. Electrical interconnection and contact to the various p or n regions that make up the integrated circuit is made by a deposition of a thin film of conductive material, usually aluminum or polysilicon, thereby finalizing the design of the integrated circuit.

Of course, the particular fabrication process and sequence used will depend on the desired characteristics of the device. Today, one can choose from among a wide variety of devices and circuits to implement a desired digital or analog logic feature.

It is not intended that the present invention be limited by the nature of the reactions carried out in the microscale device. Reactions include, but are not limited to, sequencing according to the present invention, restriction enzyme digests, nucleic acid amplification, and gel electrophoresis.

Continuous flow liquid transport has been described using a microfluidic device developed with silicon. See J. Pfahler et al., Sensors and Actuators, A21–A23 (1990), pp. 431–434. Pumps have also been described, using external forces to create flow, based on micromachining of silicon. See H. T. G. Van Lintel et al., Sensors and Actuators 15:153–167 (1988). Discrete droplet transport in silicon is also contemplated.

D) Application To Mapping Of Telomeric DNA

The present invention contemplates that the above-described sequencing method can be applied to a variety of double-stranded templates, including but not limited to telomeric DNA. Telomeres are special DNA structures at the ends of eukaryotic chromosomes, which are necessary for genome stability. In humans telomeres progressively shorten during somatic cell proliferation, perhaps eventually leading to chromosome instability. The rate and extent of shortening depends upon the type of tissue, and individual factors such as genetic background, age, and medical condition.

In human germ line and tumor cells, telomere metabolisis is different from that of somatic cells, leading to stabilization of the length of telomeres, which is believed to be due to de novo extension of 3' overhangs by the enzyme telomerase recombination, and perhaps other factors such as nucleases. Currently, the only parameter of telomere structure that can be measured is the length of the terminal restriction fragments. Measurements of the rate of telomere shortening cannot be performed in human tissues in less that ten years, or in selected human cultured cells in less than one month. Telomere shortening in most plants and animals cannot be measured due to excessive telomere length. The only existing test of the state of an individual's telomeres is a PCR assay of the in vitro telomerase activity, which is correlated with cell proliferation but not a measure whether telomeres are eroding or growing.

The present invention contemplates that the sequencing method of the present invention can provide a quantitative mapping of the DNA structure at the ends of telomeres. Indeed, preliminary results from the use of the novel sequencing method reveals long 3' overhangs at the ends of human chromosomes, suggesting a third important factor for regulating telomere length and function. The present invention contemplates that such mapping allows for the diagnosis of chromosome instabilities caused by telomerase, nucleases, recombination, and other effects important to aging and cancer.

DETAILED DESCRIPTION OF PREFERRED EMBODIMENTS

The strand replacement method of the present invention can be used to sequence a variety of templates. Such templates, include, but are not limited to, circular double-stranded templates and linear double-stranded templates produced by restriction or PCR amplification.

A. Parallel Sequencing Of Multiple Restriction Fragments From Circular DNA

Figure 2:
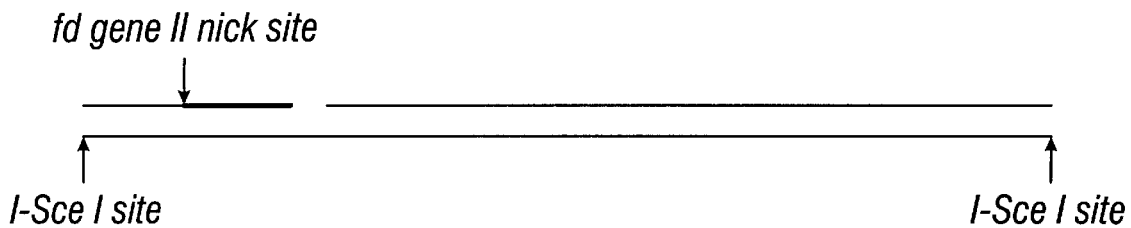
FIG. 2 schematically shows a strand-specific nick of a double-stranded template to initiate the strand replacement reaction of the present invention.
Figure 3:
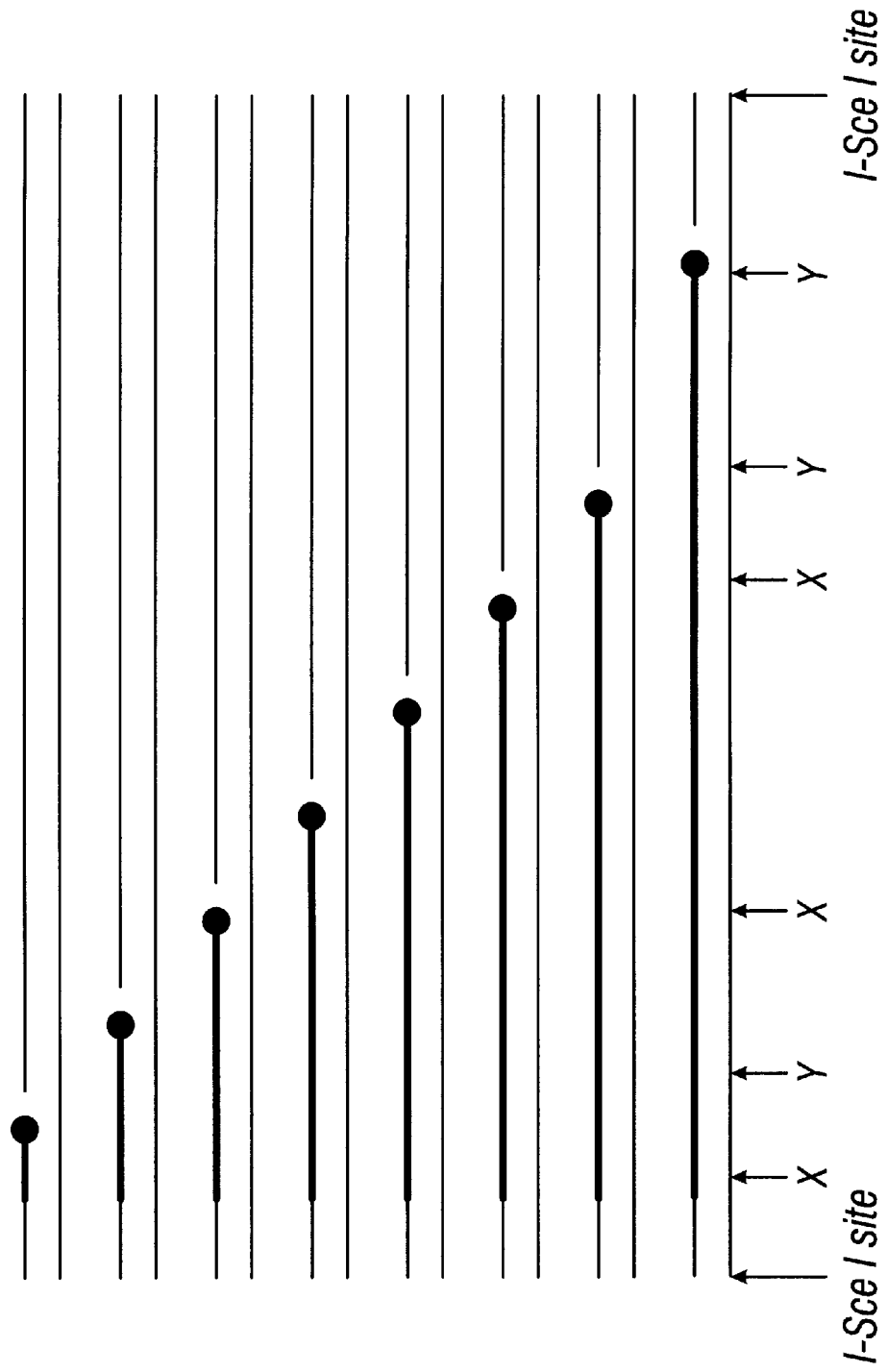
FIG. 3 schematically shows the products of the stand replacement method when carried out in the presence of termination nucleotides and the optional step of restriction digestion.

One embodiment of the invention is schematically shown in FIGS. 1–3. In this embodiment, the DNA to be sequenced is cloned into a special vector having the following features: 1) a relatively rare restriction site (I-Sce I sites) on each side of the insert, 2) a single nick site (f1 gene II site) on one side of the insert such that the 3' end of the nick is oriented toward the insert, and 3) the insert (i.e. the DNA to be sequenced). In this embodiment, no oligonucleotide primer is used.

The f1 gene product II (hereinafter "gpII") produces a sequence specific, strand-specific nick that can prime DNA synthesis by E. coli pol I [Meyer and Geider, "Bacteriophage fd gene II-protein. I. Purification, involvement in RF replication, and the expression of gene II," J. Biol. Chem. 254:12636 (1979)]. This process requires a core sequence of about 50 bp on the template DNA [Dotto and Zinder, "Reduction of the minimal sequence for initiation of DNA synthesis by qualitative or quantitative changes of an initiator protein," Nature 311:279 (1984)]. In the presence of 5 mM Mg, gpII nicks about 50% of supercoiled plasmid and relaxes the other half. The entire f1 intergenic region is the origin of replication of f1 phage, and has been cloned into a number of commercially available vectors (e.g. pSPORT available from Life Technologies). A mutant gpII (G73A) has been cloned, overexpressed, and studied [Higashitani et al., "A single amino acid substitution reduces the superhelicity requirement of a replication initiator protein," Nucleic Acds Res. 30:2685 (1992)]. This mutant protein has a relaxed requirement for plasmid supercoiling, produces mainly nicks rather than relaxed circles, and binds more cooperatively to the core site.

The plasmid (see FIG. 1) is first digested with an enzyme (e.g., the f1 gene II product) which makes a strand-specific nick (ie., a nick at one site on one of the stands of the double-stranded plasmid) at a specific recognition sequence, and then digested with the restriction enzyme corresponding to the restriction sites (e.g., I-Sce I which is a commercially available 18-base specific restriction enzyme). Taq polymerase, DATP, dTTP, dGTP, and dCTP along with optimized concentrations of the four labeled (e.g. fluorescently-labeled) dideoxyribonucleotides ddATP*, ddTTP*, ddGTP*, and ddCTP* are added and a strand replacement reaction is begun to synthesize a new DNA strand (shown bold in FIG. 2) complementary to one strand of the template DNA. Whenever a ddNTP is incorporated into the DNA, the chain is terminated and labeled with the ddNTP complementary to the one strand of template (shown as large dots in FIG. 3). This produces a distribution of double-stranded fragments, shown in FIG. 3. These molecules are then denatured and a sequencing ladder generated using standard automated sequencing gels and ddNTP detection systems.

In the case where the insert is too long to be sequenced on a single gel, the I-Sce I fragment can be cleaved (after reaction with Taq DNA polymerase) using other restriction enzymes. In the case shown in FIG. 3, two restriction enzymes (X and Y) produce eight restriction fragments to be sequenced. The overlapping sequences from the resolved restriction fragments will determine the entire sequence of the insert. Note that the restriction fragments can be resolved on double-stranded gels as bands of discrete length. The ability to fractionate DNA according to length is not affected by the presence of nicks in the double-stranded DNA. As noted above, it is well-known that double-stranded DNA with nicks or other flexible joints forms sharp bands during electrophoresis [Higashitani et al., "A single amino acid substitution reduces the superhelicity requirement of a replication initiator protein," Nucleic Acds Res. 30:2685 (1992)]. Only at the step that a denaturing sequencing gel of each restriction fragment is performed will a ladder of bands at single-base intervals be produced.

Alternative procedures could be used for many of the steps. The strand replacement reaction could be performed by a different polymerase, such as E. coli polymerase I. The restriction fragments produced by enzymes X and Y could be separated by capillary or slab electrophoresis. The ddNTP-terminated nucleic acids could be labeled with different colored dyes or with radioactivity.

An example of the steps necessary to do the sequencing of a large insert would be: 1) make the nick with f1 gene II product and cleave with I-Sce I; 2) add polymerase (e.g., Taq DNA polymerase) and nucleotide triphosphates (dNTPs and ddNTPs) for a fixed time; 3) restrict half of the sample with enzyme X and the other half with enzyme Y; 4) in parallel, separate the X and Y restriction fragments by capillary electrophoresis; 5) denature each of the isolated restriction fragments and sequence in a conventional sequencing apparatus. Steps 1–3 can be performed successively in the same tube. In principle, steps 4 and 5 could be done automatically within the sequencing device.

B. Parallel Sequencing Of Multiple Restriction Fragments From Linear DNA

Figure 4A:
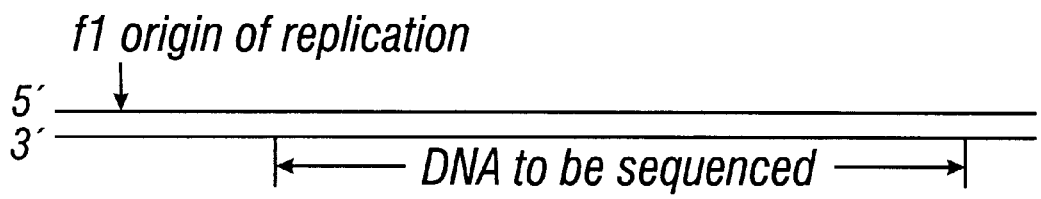
Figure 4B:
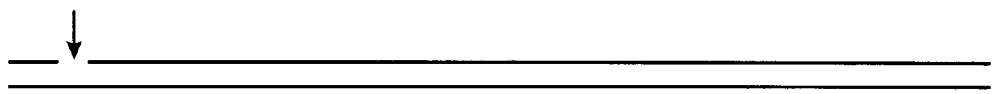
Figure 4C:
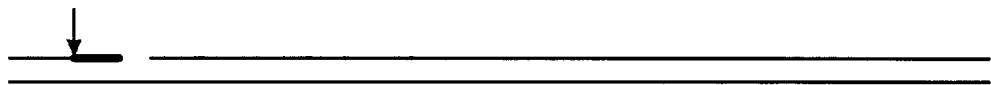
Figure 4D:
Figure 4E:
Figure 4H:
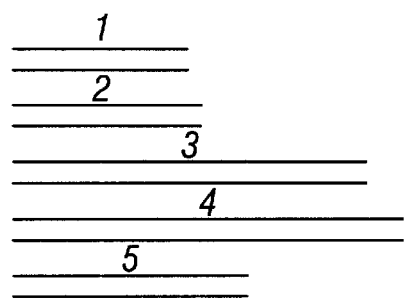
Figure 4I:
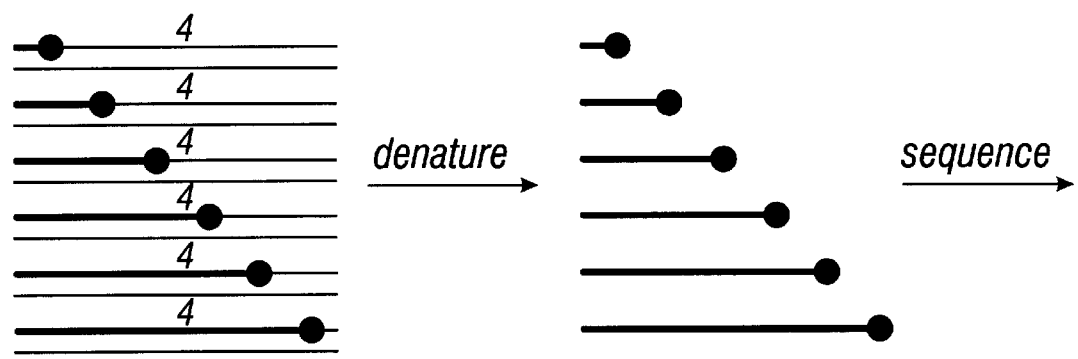

In one embodiment, the strand replacement method of the present invention is used to map the positions of bases along DNA of multiple restriction fragments. A double stranded DNA template is used (FIG. 4A). A nick is made in one of the strands (FIG. 4B). A strand replacement reaction is initiated (FIG. 4C). The products are generated in the presence of termination nucleotides (4 dNTPs) (FIG. 4D) and elongation is thereby terminated (FIG. 4E). The products represent nucleic acid terminated at different sites (e.g. different adenine sites) (FIG. 4F). Two restriction endonuclease cleavage reactions of the products are performed with different enzymes (X and Y) (FIG. 4G). The restriction fragments are fractionated according to size (FIG. 4H). Thereafter, each fragment can be denatured and sequenced (FIG. 4I, illustrative results are shown for strand #4 from FIG. 4H) using conventional denaturing sequencing gels.

C. Sequencing DNA Adjacent To A Series Of Restriction Sites

Figure 5:
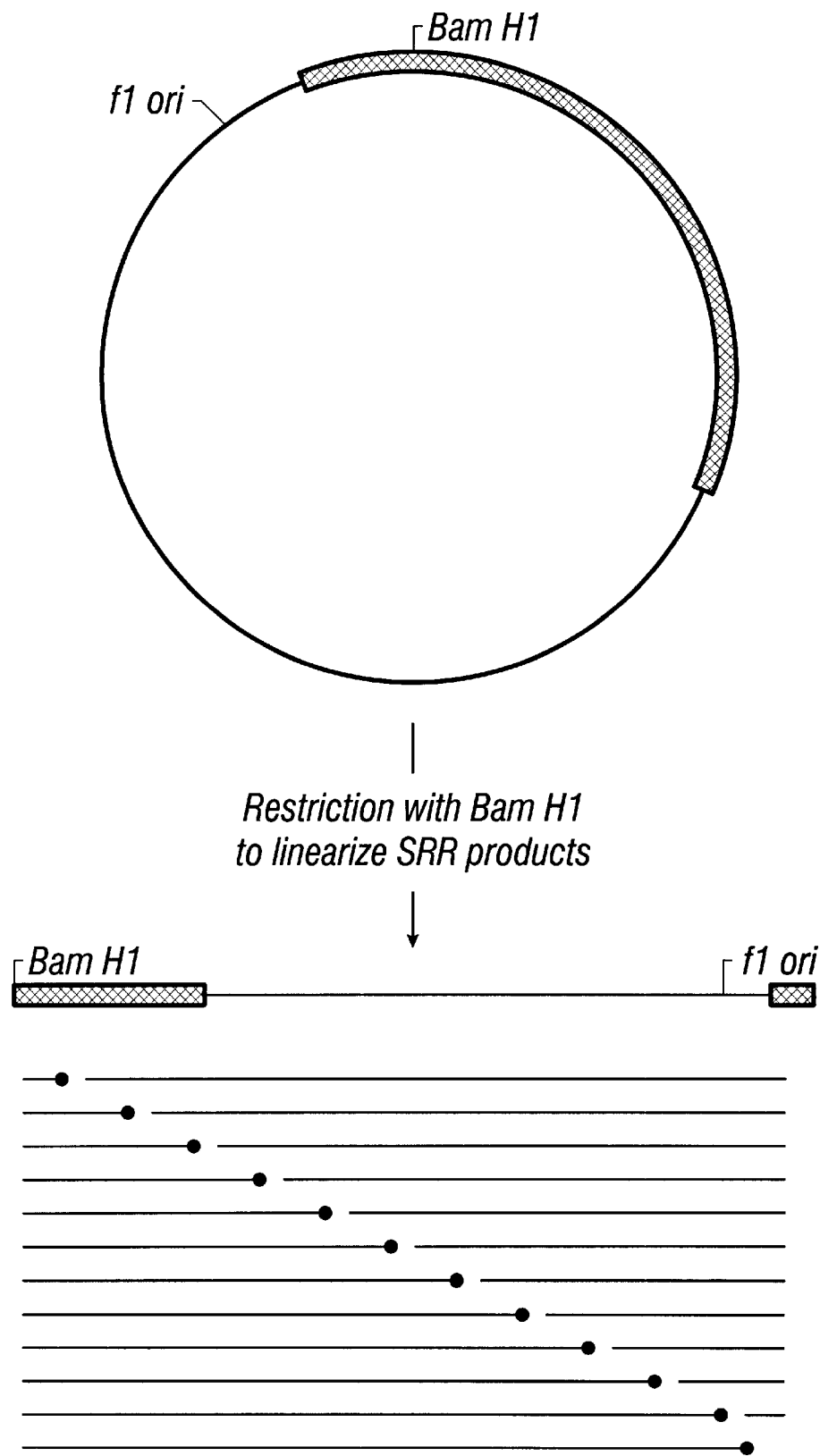
FIG. 5 schematically shows one embodiment of the strand replacement method of the present invention whereby sequencing can be performed directly on restriction fragments, without size fractionation.

In certain cases, expected to occur often in DNA molecules less than about 5 kb in length, a number of restriction enzymes can be found that will cleave the DNA only once within the unknown sequence. In these cases only one restriction fragment will be formed, and sequencing can be performed directly, without size fractionation. This is illustrated in FIG. 5 for a circular plasmid having an insert containing a single Bam H1 site. Strand replacement begins at the nick site (f1 origin site) and proceeds clockwise. By making nicks in different strands, the sequences adjacent to the restriction sites in both directions can be determined. A single strand replacement product can be subjected to digestions with different restriction enzymes. The products from each restriction digestion can be subjected to sequencing reactions to get sequence information from many sites. For example, after linearization with the restriction enzyme Bam H1, the products can be sequenced starting from the Bam H1 site. This method will also work with linear DNA as long as the end of the DNA behind the strand replacement polymerization is long enough (e.g. >1000 bp), such that the synthesized strand containing the sequences of the f1 origin are too long to interfere with the bands produced adjacent to the restriction site.

D. Bidirectional Sequencing Adjacent To A Series Of Restriction Sites

In another embodiment, both sides of a single internal restriction site (clockwise and counterclockwise) are sequenced in a covalently-closed circular DNA molecule. In the presence of ethidium bromide [Kovacs et al., "The generation of a single nick per plasmid molecule using restriction endonucleases with multiple recognition sites," Gene 29:63 (1984)] many restriction endonucleases are able to nick DNA at the recognition site. After the initial nick, no further digestion takes place, so that most molecules have a single nick. Half of the molecules will have a nick in the top strand, and the other half a nick in the bottom strand. After removal of ethidium bromide using standard techniques, the mixed population of DNA molecules is subjected to the strand replacement sequencing reaction of the present invention. Those molecules nicked in the top strand will synthesize products in a clockwise direction; those nicked in the bottom strand will synthesize products in the counterclockwise direction. Those rare molecules that are not nicked or have undergone double-strand scission will not initiate the SR reaction. By controlling the reaction time the strand replacement sequencing reaction will be allowed to proceed long enough to progress about twice the critical length for sequencing by gel electrophoresis (~2,000 bp). Some of the strands will terminate at ddNTP sites and others will terminate at ~2,000 bp (for example).

Alternatively after removing the ethidium bromide, the template DNA can be restricted at a rare restriction site located far from the insert that is being sequenced (the external restriction site). After the SR reaction, the products are cleaved again with the first restriction site, which cuts at the internal site, and also at the external site (if not cut previously). Now the sample consists of a mixture of two double-stranded restriction fragments, one carrying the strand replacement products synthesized clockwise from the internal restriction site and the second carrying the strand replacement products synthesized counterclockwise from the same internal restriction site. In principle, these fragments can be separated by molecular weight; however, because it is a binary mixture, any of a number of simpler, affinity techniques could be used. For example, the vector sequence to the left of the DNA insert can contain a sequence that will bind to a special triplex forming oligonucleotide or other sequence-specific DNA binding molecule [Hacia et al., "Inhibition of Klenow fragment DNA polymerase on double-helical templates by oligonucleotide-directed triple-helix formation," Biochemistry 33:6192 (1994); Pilch et al., "Binding of a hairpin polyamide in the minor groove of DNA:sequence-specific enthalpic discrimination" Proc. Natl. Acad. Sci. USA 93:8306 (1996); Trauger et al., "Recognition of DNA by designed ligands at subnanomolar concentrations," Nature 382:559 (1996)] that contains a chemical tag that can be affinity immobilized. The chemical tag allows for immobilization of the DNA binding molecule and attached DNA (in this case, the double-stranded restriction fragment to the left of the restriction site). In the case of a specific tag, such as a triplex-forming biotinylated oligonucleotide, one of the two double-stranded DNA molecules can be immobilized on a strepavidin-coated surface (e.g. beads). The free DNA can be loaded on the one lane of a sequencing gel and analyzed to sequence the bases located clockwise from the internal restriction site; the immobilizing surface (e.g. beads) can be washed to remove unbound DNA, denatured, and loaded on a different lane of the sequencing gel. Such separation has been used previously to separate strands of denatured PCR-amplified DNA before conventional ddNTP sequencing reactions [Hultman et al., "Bi-directional solid phase sequencing of in vitro amplified DNA sequences," BioTechniques 10:84 (1990); Lagerqvist et al., "Manifold sequencing: Efficient processing of large sets of sequencing reactions," Proc. Natl. Acad. Sci. USA 91:2245 (1994)}.

E. Ligation-Mediated Initiation Of Strand Replacement DNA Sequencing

Figure 6:
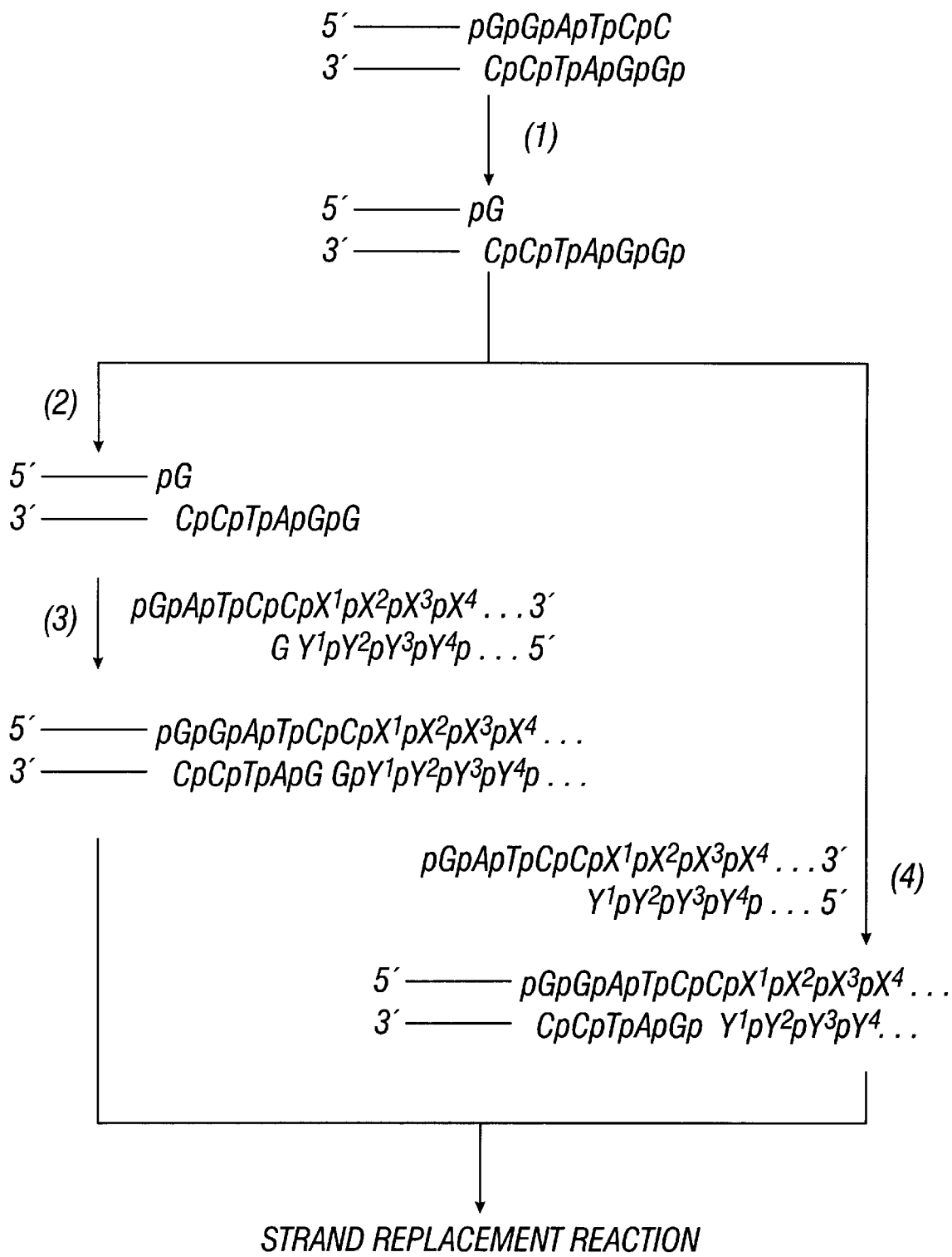
FIG. 6 schematically shows one embodiment of the ligation-mediated method of the present invention for initiation of strand replacement DNA sequencing.

Linear restriction fragments can be produced by restriction of cloned or PCR amplified DNA (FIG. 6, step 1). For illustrative purposes, the DNA in FIG. 6 has been cleaved with Bam HI at one end. To create an initiation point for strand replacement at one end of such a molecule, a special double-stranded adaptor DNA molecule is ligated to one end of the restriction fragment using a ligase (including, but not limited to *E. coli* ligase or T4 ligase) in such a fashion that a nick or one base gap is formed. This is achieved, for example, by dephosphorylating the 5' ends of the restriction fragment (for example with calf intestinal phosphatase or shrimp alkaline phosphatase) before the ligation reaction (FIG. 6, steps 2 and 3), or by using a double-stranded oligonucleotide (FIG. 6, step 4) designed with a 3' end one base shorter than required for ligation. The 3' OH within the resulting nick or gap serves as the initiation point for the strand replacement reaction. Sequence information can be gained by analysis of the strand replacement products starting from one terminus or the other, using different nicking strategies for the two ends. In addition, cleavage with different restriction enzymes will allow sequencing to be "read" adjacent to different restriction sites.

F. Sequencing Of PCR Products

Figure 7A:
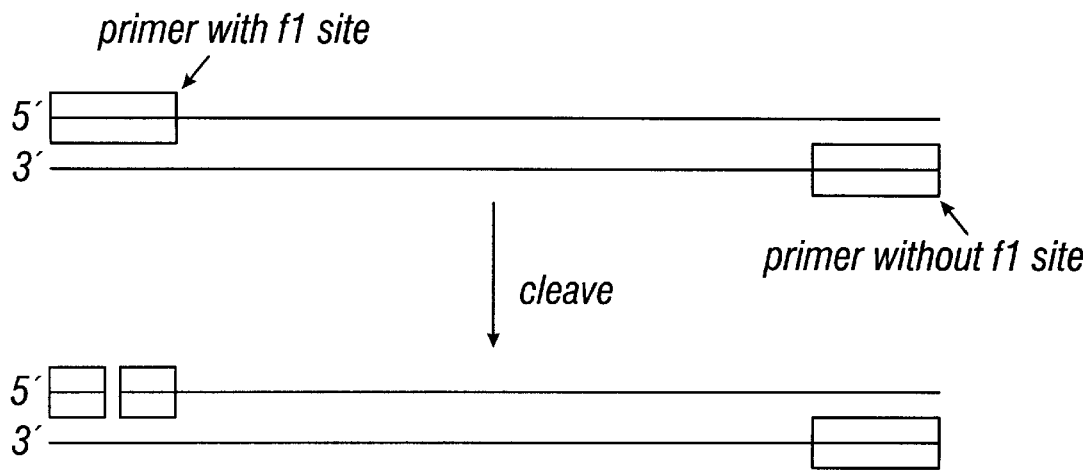
FIGS. 7A through 7D schematically shows one embodiment of the strand replacement method of the present invention for sequencing PCR products.
Figure 7B:
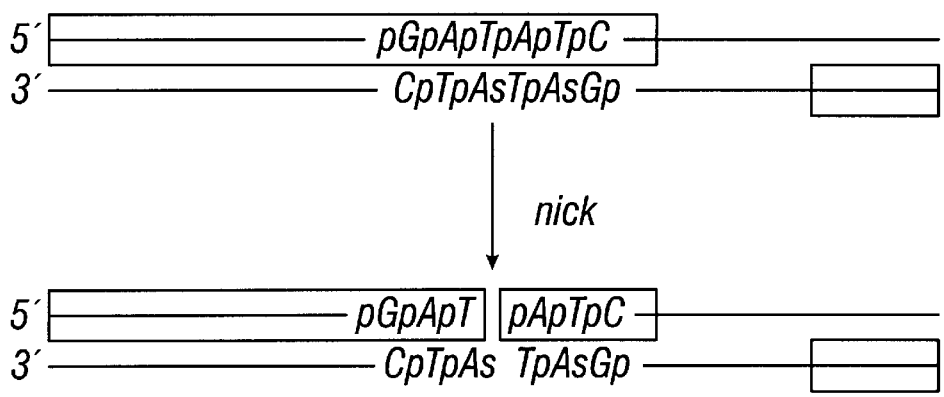
Figure 7C:
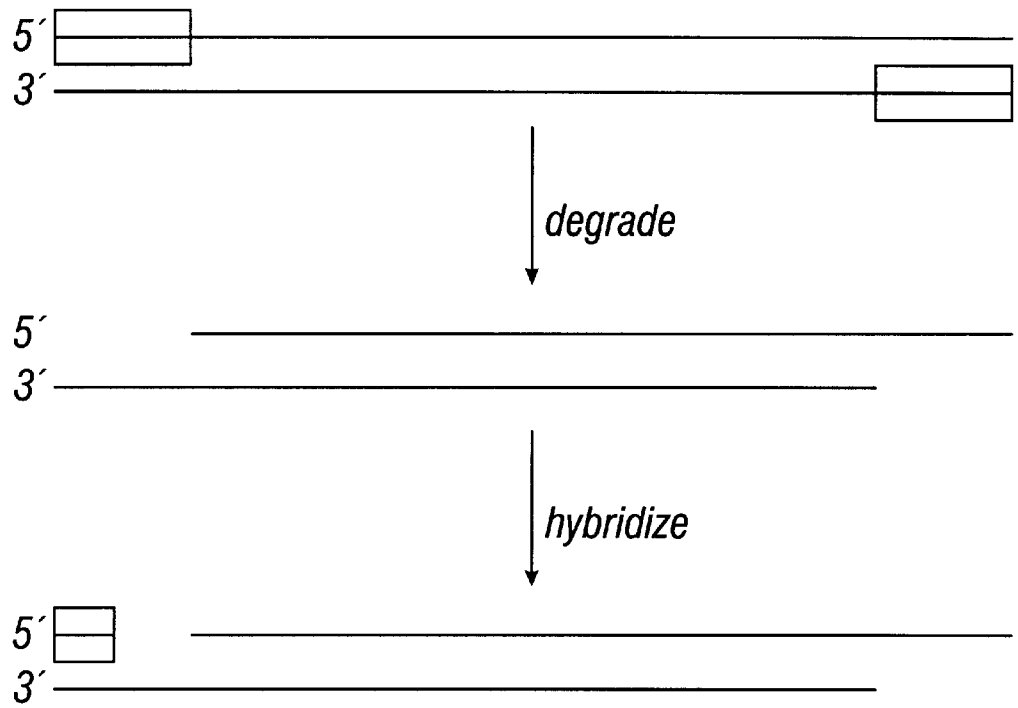
Figure 7D:
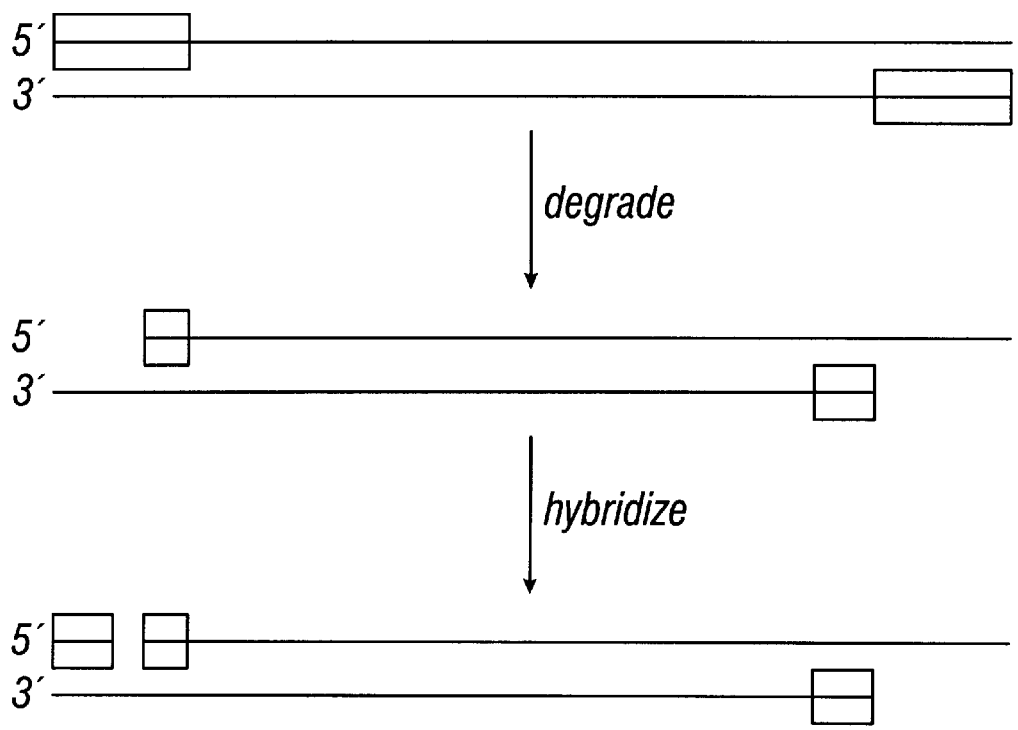

PCR products can be subjected to the strand replacement method of the present invention. In one embodiment, PCR products are sequenced by incorporating special oligonucleotide primers for the PCR reaction that can be later processed to form a nick. For example, one of the two PCR primers can contain an f1 origin core sequence which can be cleaved with gpII (FIG. 7A). Alternatively, the PCR products can be subjected to treatments to degrade a few nucleotides from the 5' termini [e.g., by use of T7 gene 6 exonuclease (FIG. 7C), or by cleavage of dUTP present in one of the primers (FIG. 7D)]. Subsequent hybridization of an oligonucleotide primer under non-denaturing conditions to the 3' tail of the PCR products will produce the priming site necessary for initiation of strand replacement.

Alternatively, an assymetr PCR reaction can incorporate a phosphorothiolated nucleotide analog into one of the two DNA strands. Certain restriction enzymes are known to nick the normal strand of hemiphosphorothiolated DNA [Olsen et al., "Investigation of the inhibitory role of phosphorothioate internucleotidic linkages on the catalytic activity of the restriction endonuclease EcoRV," Biochemistry 29:9546 (1990)], schematically represented in FIG. 7B.

G. Mapping The Distance Of Genetic Sites From The SR Initiation Site

Often it is desirable to map sequence information in very long pieces of DNA (e.g., cosmids, YACs, and within or at the ends of intact chromosomes). The landmarks that can be mapped using long-range SR reactions include (a) specific known sequences, such as those associated with a particular genes, (b) restriction sites, (c) anonymous sequences present in a library of cloned or PCR amplified genomic or cDNA sequences, (d) repetitive sequences such as Alu repeats, CpG islands, dinucleotide and trinucleotide repeats, SINES, LINES, and telomere repeats, (e) unusual secondary structures such as triplex DNA, quadruplex DNA, cruciform DNA, and (f) specific types of lesions, such as thymidine dimers. Present techniques are unable to map these types of features because (1) many of the features are characteristic of double-stranded DNA, and (2) mapping usually requires a nearly synchronous progression of the synthesis of new DNA. Neither of these conditions seem to be met by enzymes utilizing a single-stranded template. The present invention contemplates using the strand replacement method with a highly processive SR polymerase, such as Taq DNA polymerase, for this task.

Figure 8:
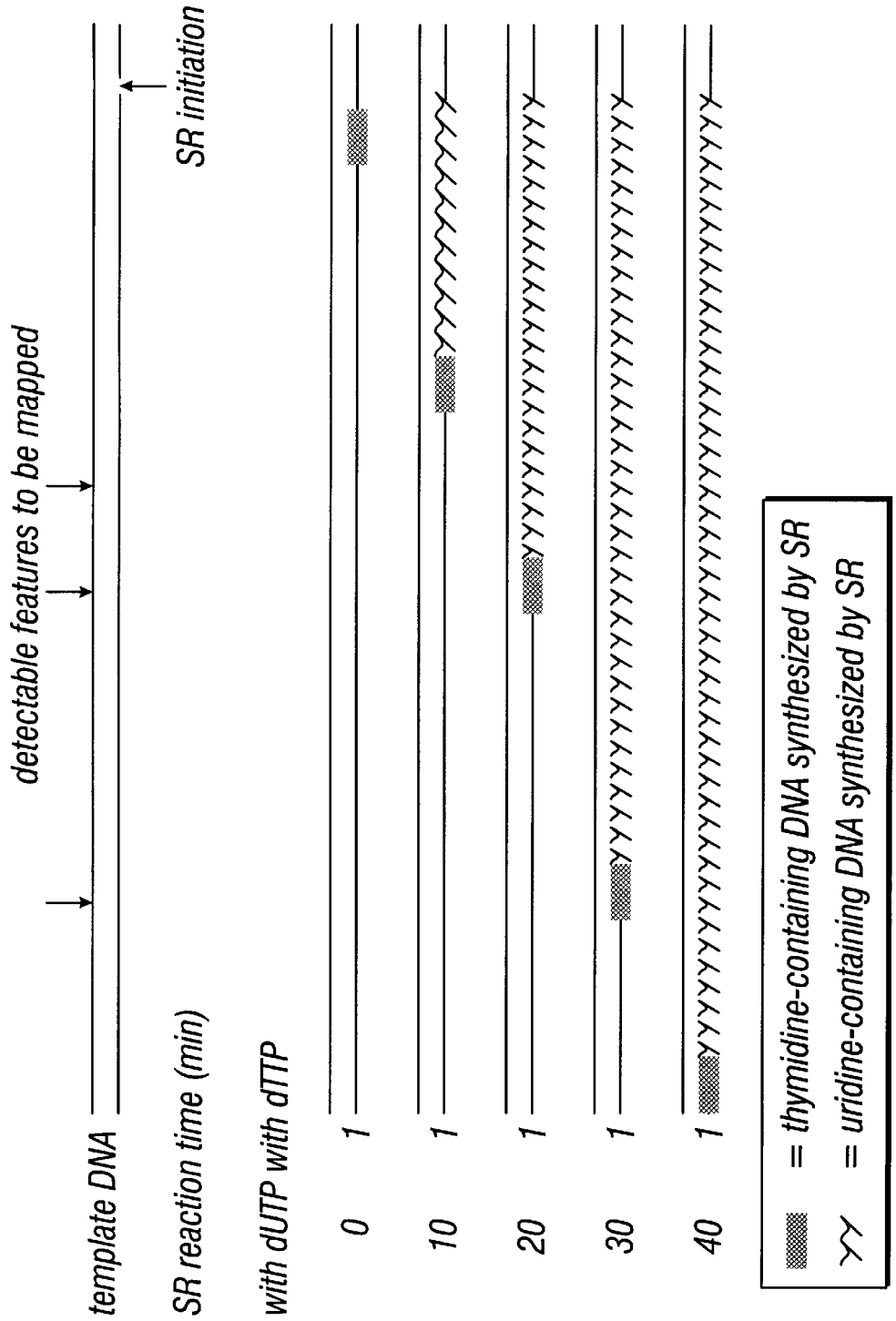
FIG. 8 schematically shows one embodiment of the strand replacement method of the present invention for mapping the distance of genetic sites from the strand replacement initiation site.

In one embodiment, SR synthesis initiates at a unique site using an excess of processive polymerase, which incorporates DATP, dGTP, dCTP, dUTP (or any other labile base) into the DNA (FIG. 8). After a controlled period of incorporation of the labile base, conditions are changed to incorporate only the stable bases DATP, dGTP, dCTP, and labeled dTTP. The dTTP can be radioactively labeled, fluorescently labeled, chemically labeled with biotin, etc. The uracil bases can be removed using dU glycosylase (Boehrenger Meinheim), and the sites efficiently converted to nicks by heating the DNA. After cleavage of the dUTP-substituted DNA, the labeled DNA from the different SR reaction times can be hybridized to a sequence of interest (e.g., telomeric sequences, dinucleotide repeats, alu sequences, cloned or PCR-amplified sequences, expressed sequences from a cDNA library, etc.). Either the strand replacement DNA or the sequences of interest can be labeled. In the example shown in FIG. 8, positive hybridization would be detected for the samples from SR reactions carried out for about 15 min, 20 min, and 30 min. If the measured rate of SR elongation was 250 nucleotides per minute, those features would be mapped as being 3.75 kb, 5.0 kb, and 7.5 kb from the initiation site. By hybridizing to restriction fragments transferred from an agarose gel, the order of the restriction fragments could be easily mapped. This information could be very useful in large-scale sequencing projects to order the restriction fragments in cosmids and YACs. As the time increases the polymerases will lose synchrony and the width of the band of stable DNA will increase, reducing resolution. To overcome this problem agents can be introduced to reversibly halt the polymerase molecules at specific sequences. When the arrest is reversed all of the polymerases will regain their initial synchrony. Triplex-forming oligonucleotides can bind to recognition sequences along DNA and can arrest the progress of Klenow fragment [Hacia et al., "Inhibition of Klenow fragment DNA polymerase on double-helical templates by oligonucleotide-directed triple-helix formation," Biochemistry 33:6192 (1994)]. The arrest by oligonucleotides should be reversed by mild heating or changes in pH.

The technique described can also be used to map features in the DNA that terminate SR, such as unusual secondary structure, triplex formation, and specific protein binding. In this case the SR reaction would be performed using DATP, dGTP, dCTP, and dTTP and the products separated by molecular weight using electrophoresis. Sites of pausing of the polymerase would be detected by increase in product concentration or the onset of hybridization to a specific DNA probe.

H. Microchip Oligonucleotide Array Sequencing

Array sequencing involves hybridizing labeled unknown DNA to an array of oligonucleotides with different sequences. If a particular sequence (e.g., TTAGGG) occurs within the DNA, the array position having the CCCTAA oligonucleotide hybridizes to the unknown DNA, thereby immobilizing the label at a specific array position. By examining which array positions become labeled, a computer is able to reconstruct the sequence of the unknown DNA. The inherent limitations of the specificity of nucleic acid hybridization make it impractical to use oligonucleotides longer than ~6 nucleotides. This leads to a practical limit to the number of nucleotides in the unknown DNA to 50–100.

Figure 9:
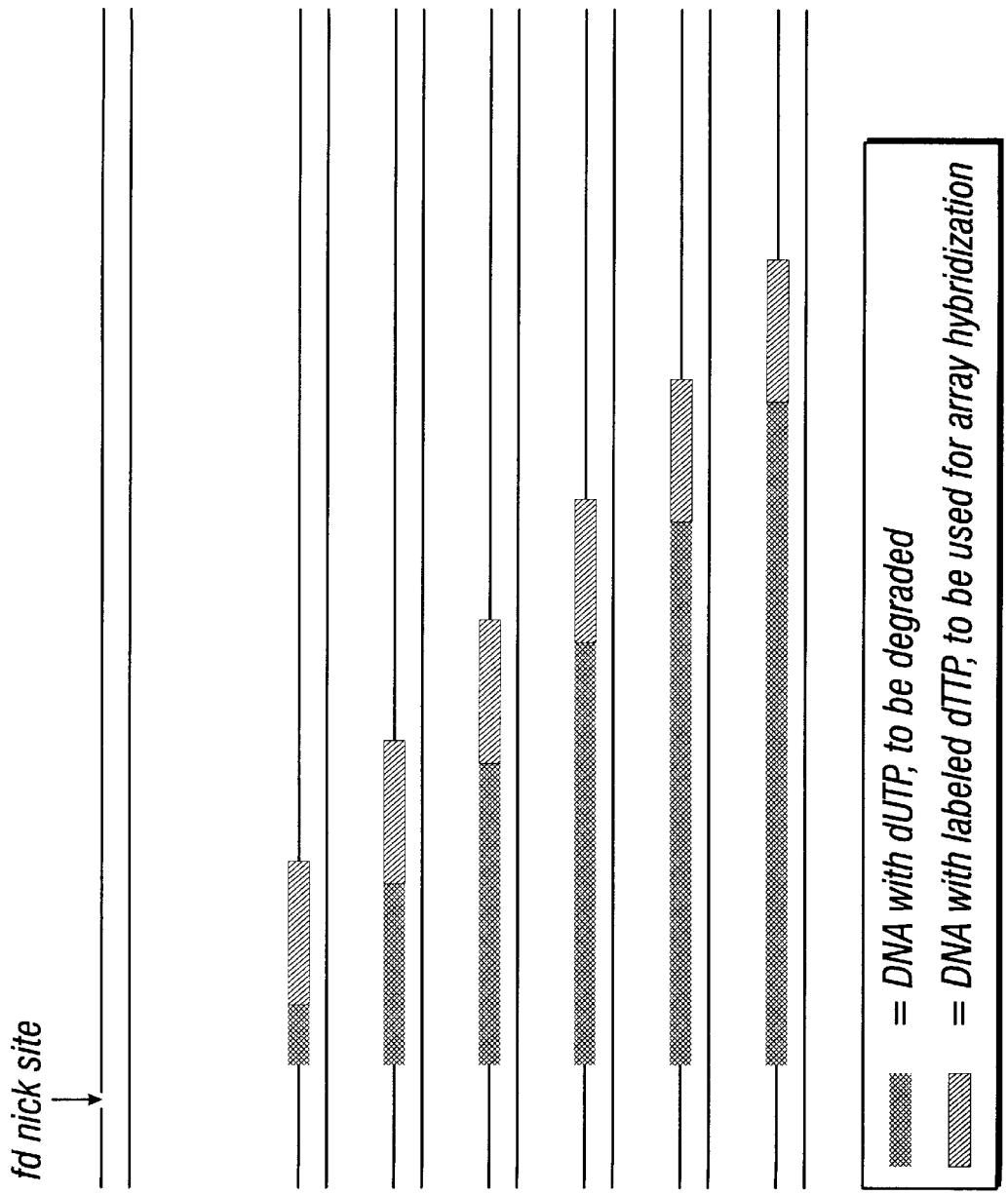
FIG. 9 schematically shows one embodiment of the strand replacement method of the present invention for producing groups of short DNA molecules at different distances from the initiation site.

The strand replacement method of the present invention provides a method for overcoming this limitation by producing groups of short DNA molecules at different distances from the gp II nick site, as shown in FIG. 9. In this figure, one embodiment of the method is shown for creating DNA different distances from the nick site. In this example, dUTP, DATP, dGTP, and dCTP are incorporated during an initial, variable period of the strand replacement reaction, followed by a fixed-time pulse of incorporation of dTTP, DATP, dGTP, and dCTP. The dTTP preferably is labeled (e.g., a radioactive label, a fluorescent label, or other suitable label). The incorporation of dUTP is done for variable times, whereas incorporation of dTTP is for a constant time, designed to allow synthesis of a stable oligonucleotide short enough to be used for oligonucleotide array sequencing located specific distances from the f1 nick site. After the strand replacement reaction, the dU bases are destroyed with deoxyribouracil glycosylase and heat, leaving the different samples of short, labeled nucleic acid bases to be sequenced on the microchip oligonucleotide arrays. This specific embodiment can be generalized to sequence DNA different distances from any strand replacement initiation site.

EXPERIMENTAL

The following examples serve to illustrate certain preferred embodiments and aspects of the present invention and are not to be construed as limiting the scope thereof. In some of the examples below fibroblasts were used. For these experiments, three derivative cultures of female human fetal lung fibroblasts were purchased and grown strictly according to instructions from the NIA Aging Cell Repository (Coriell Institute for Medical Research, Camden, N.J.). Normal IMR-90 primary cells (catalog #190 P04 and #190 P10, after 4 and 10 laboratory passages) and post-crisis immortal SV40 virus-transformed IMR-90 (#AG02804C) were harvested at about 80% confluence. The IMR-90/P04 and IMR-90/P10 cells were harvested after −33 and −63 post-fetal population doubling, respectively.

In some experiments human umbilical vein endothelial (HUVE) cells and human leukocytes were used. HUVE cells were grown as described (Dixit, V. M., et al. (1989), J. Biol. Chem. 264, 16905–16909.) and harvested after 11 passages. Human leukocytes were separated from fresh blood by isotonic lysis (Birren, B., et al. (1993), Pulsed field gel electrophoresis: a practical guide. (San Diego: Academic Press).). 1–2×$10^8$ cells were harvested by centrifuging 3× for 10 min at 800×g in 15 ml cold PBS followed by resuspension in PBS (~12×$10^8$/ml).

A number of the examples below involve the use of nucleic acid isolated from nuclei. Nuclei were prepared using centrifugations at 4° C. as above: 1–2×$10^8$ washed cells were centrifuged once in 15 ml of nuclear buffer (60 mM KCl, 15 mM NaCl, 15 mM HEPES pH 7.4, 3 mM $MgCl_2$, 6 µM leupeptin, 1 mM iodoacetate, 1 mM phenyl-methyl sulfonyl fluoride), once in 1.5 ml nuclear buffer, twice in 15 ml nuclear buffer with 0.1% digitonin, and once in nuclear buffer with digitonin without iodoacetate; nuclei were resuspended in 1 ml of nuclear buffer without iodoacetate, diluted to $10^7$ cells/ml with nuclear buffer without iodoacetate prepared with 50% glycerol, and frozen in liquid $N_2$.

A variety of commercially available reagents were employed. Tissue culture supplies were from Sigma (St. Louis); restriction enzymes, S1 nuclease, DNA polymerase I, T4 DNA ligase, and random labeling kit from GibcoBRL; Hinf I from BioLabs; Bal 31 nuclease, T4 DNA polymerase, dU-glycosylase, proteinase K and Agarase from Boehrenger Meinheim; Klenow fragment (exo) from Ambio; T7 gene 6 exonuclease from Amersham/USB; agarose from Gibco-BRL and FMC; ZetaProbe GT membrane and PCR rules from BioRad; radioisotopes from Amersham. Oligonucleotides were synthesized at the University of Michigan Biomedical Research Core Facility. Oligonucleotide $(CCCUAA)_4(TelC)$ was used as a primer for strand replacement reactions. Oligonucleotides $(CCCTAA)_3CCC$, $(UUAGGG)_4(TelG)$, $CCCTCCAGCGGCCGG(TTAGGG)_3$ and $(CCCUAA)_4$ were used for probe preparation.

For DNA purification, a protocol for isolation of high molecular weight DNA in solution was used (Birren, B., et al. (1993), Pulsed field gel electrophoresis: a practical guide. (San Diego: Academic Press). Tissue culture and fresh blood cells were washed 3 times at 800×g in PBS, and $10^8$ washed cells were resuspended in 0.5 ml PBS. Then 0.125 ml 20 mg/ml proteinase K solution, 1.625 ml 0.25 M EDTA, pH 8.0, and 0.25 ml 10% SDS were added in the indicated order, gently mixed and incubated at 50° C. Frozen nuclei were washed three times with nuclear wash buffer (15 mM NaCl, 15 mM Tris-HCl pH 7.5, 60 mM KCl, 3 mM $MgCl_2$), resuspended at 300–400 μg/ml, and gently mixed with an equal volume of digestion buffer (30 mM Tris HCl pH 7.5, 100 mM EDTA pH 8, 2% SDS, 2 mg/ml proteinase K), and placed at 50° C. Equal amounts of fresh proteinase K solution were added every 12 h, and incubation continued to 36 h. DNA was extracted with buffered phenol, followed by phenol/chloroform and chloroform extractions. The clear, viscous DNA solutions were dialyzed against TE. DNA concentrations were determined by spectrophotometry (usually 100–200 μg/ml) and DNA solutions were stored at 4° C. for several months without detectable loss of integrity. For certain critical experiments (e.g. for G-overhang length analysis) the DNA was digested with RNase. Telomere molarity was calculated assuming $75 \times 10^6$ bp per telomere (or $3.4 \times 10^9$ bp per haploid genome).

EXAMPLE 1

Oligonucleotide Primer Dependent Strand Replacement On Double-Stranded Template Having Single-Stranded Regions Created By Nuclease Digestion Telomere DNA is difficult to sequence due to the repetitive sequences involving DNA strands that are either rich in guanine or cytosine. Single-stranded GC rich DNA forms intramolecular and intermolecular secondary structure that causes premature termination of DNA polymerization. In addition, G-rich DNA is able to form non-Watson-Crick hydrogen bonding involving G:G base pairs that are often more stable than Watson-Crick double-stranded DNA. In vitro, single-stranded G-rich telomere DNA can form a variety of non-canonical structures including G-quartets, triple helices and G:G base pairing.

In this example, the primer-dependent strand replacement method of present invention was used to measure human telomere DNA. FIG. 10 shows the strand replacement approach as applied to the detection and quantitation of G-tails in human chromosomes. The oligonucleotide $(CCCTAA)_4$ (TelC) is hybridized under non-denaturing conditions to available G-rich tails and extended using Taq polymerase. The polymerase fills the gap between the primer and 5'-end of the C-strand and then propagates the nick in the 3' direction. If several molecules of TelC bind to the overhang, all but the last one will be degraded during the reaction. When electrophoresed on a denaturing alkaline agarose gel and probed with both the G-rich and C-rich telomeric sequences, the reaction products should appear as three bands: $C_s$ corresponds to the newly-synthesized extension products; $C_t$ corresponds to the trimmed original C-rich strands; and $C_o$ corresponds to the original G-rich strands and untrimmed C-rich strands from any telomeric ends without overhangs or with such short overhangs that they cannot bind the primer.

In this example, the reaction was carried out on a model linear telomere construct. The construct with 520–700 bp of double-stranded human telomere DNA and 100–200 b of G-rich overhang was constructed from plasmid Sty11. Sty 11 was cut with ClaI which leaves 10 bp of polylinker DNA at the end of a 800 bp telomere tract. The linearized plasmid was digested with Bal 31 for 30 seconds at 30° C. using 2 units of enzyme with 10 μg DNA in 100 μl of 600 mM NaCl, 12.5 mM $CaCl_2$, 12.5 mM $MgCl_2$, 20 mM Tris-HCl pH 8.0, and 1 mM EDTA. The DNA was extracted and resuspended in TE. EcoR I restriction and electrophoretic analysis determined that the Bal 31 had trimmed about 60 bp from each end, sufficient to expose the relomeric repeat. To produce a 3' overhang 5 μg of linearized or linearized/Bal 31 treated DNA was incubated with 100 units of T7 gene 6 exonuclease in 50 μl of 40 mM Tris-HCl pH 7.5, 20 mM $MgCl_2$, 50 mM NaCl at 20° C. for different times, extracted, and resuspended in TE. The average G-tail length and length distribution were determined by digestion with EcoRI, electrophoresis in 1.5% agarose/40 mM NaOH and analysis of the length of the C-strand. It was determined that, following the above treatment, one end of the construct had a 650 bp terminal tract of double-stranded telomeric DNA with a 100 b G-tail.

The strand replacement reaction was performed using Taq DNA polymerase. The optimized reaction was performed in 50 μl of the standard Taq polymerase buffer [composed of 20 mM Tris-HCl pH 8.3, 50 mM KCl, and 2 mM $MgCl_2$ containing 50 μM dNTPs, 5–10 nM TelC primer, 0.1–1 fool of DNA telomere ends (5–50 μg of human DNA or 0.1–1 ng of Sty11 telomere construct) and 2 units of Taq polymerase] and was carried out at 55° C. To insure the hybridization of the TelC primers to all single stranded telomere ends, the ingredients of the reaction (except Taq polymerase) were placed into 0.5 ml thin-wall PCR tubes, mixed, covered with mineral oil, and incubated at 45° C. for 1 h in a DNA Thermal Cycler 480 (Perkin-Elmer, Cetus). The temperature was increased to 55° C. for 5 min, and Taq DNA polymerase was added. Aliquots were removed at the desired times and quenched on ice with 10 mM EDTA. All DNA samples were incubated with dU-glycosylase (1 μl enzyme 50 μl reaction) at 37° C. for 1–2 h, ethanol precipitated, washed and dried. The dU-glycosylase promoted primer degradation during alkaline electrophoresis, greatly reducing the background on Southern blots.

Figure 11A:
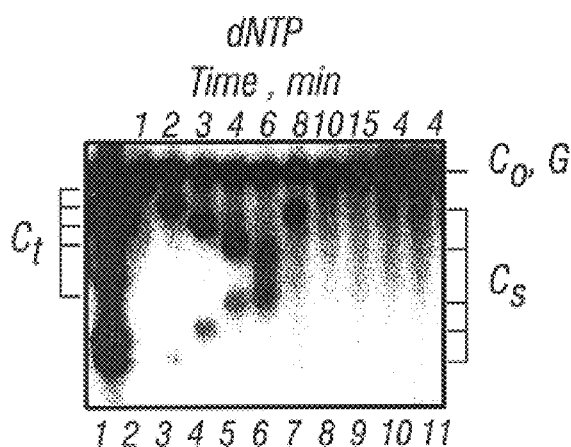
FIGS. 11A through 11D show the detection by electrophoresis of G-rich tails on the model telomeric construct of FIG. 10 using one embodiment of the strand replacement method of the present invention.
Figure 11B:
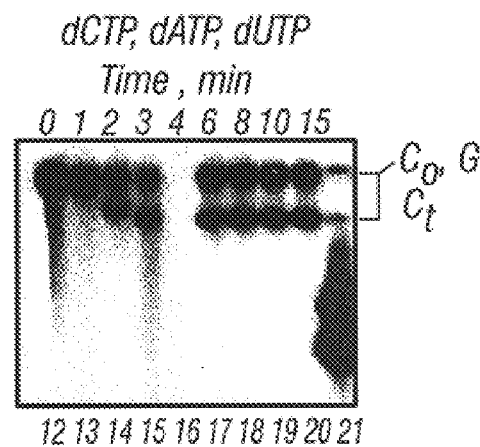
Figure 11C:
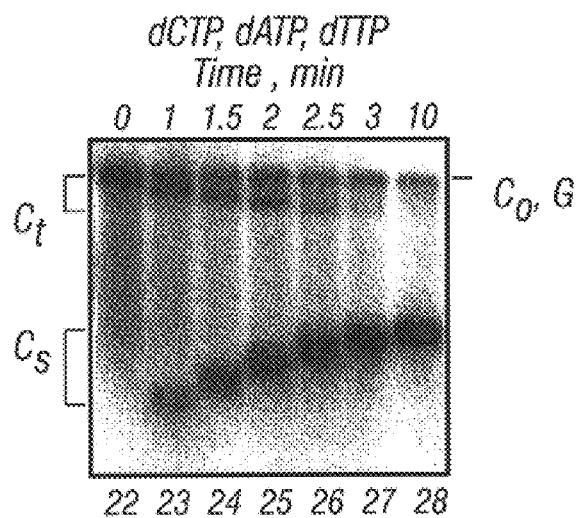

FIGS. 11A, 11B, and 11C show the results of the strand replacement reaction using the model construct. The size of the $C_s$ strand increased at the same rate as the size of the $C_t$ strand decreased, ruling out strand displacement (Henderson, E. R., et al. (1988), Cancer Cells 6, 453–461.). In the presence of four dNTPs the nick-translation reaction proceeded to the opposite end of the linear construct (FIG. 11A, lanes 2–9). In the presence of only DATP, dTTP and dCTP the reaction proceeded only to the end of the telomeric tract, producing a discrete 750 b C-rich strand (FIGS. 11B and 11C). Substitution of dTTP with dUTP and incubation of the reaction products with dU-glycosylase followed by alkaline treatment led to complete elimination of the $C_s$ strand (FIG. 11B). After long reactions the $C_t$ strand hybridized with the random-primed plasmid (FIGS. 11A and 11B), but not $(TTAGGG)_4$ (TelG) (FIG. 11C).

Figure 11D:
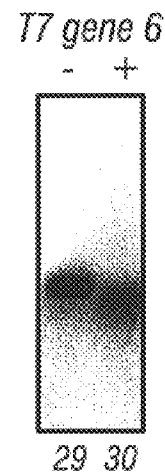

A 100 b overhang is long enough to initiate multiple strand replacement reactions, however the terminal $C_s$ strand should destroy and replace internally-located primers and products. Thus the $C_s$ product made without dGTP (FIG. 11C, lane 28) had the same size as the C-rich fragment without T7 gene 6 treatment (FIG. 11D, land 29). No strand replacement products were found (a) without primers (FIG. 11A, lane 10), (b) with TelG primers (not shown), (c) with non-telomeric primers (not shown), or (d) on constructs without G-tails (FIG. 11A, lane 11).

In sum, the strand replacement signal is dependent upon the presence of the TelC primer showing that products are not formed from internal nicks or gaps. In the model system, the strand replacement reaction with (TTAGGG) overhangs is specific for a primer containing the (CCCTAA) repeat, and blunt-ended telomeric ends are not detected.

EXAMPLE 2

Oligonucleotide Primer Dependent Strand Replacement On Double-Stranded Template Having Naturally Occurring Single-Stranded Regions In this example, the strand replacement method was used to detect naturally occurring single-stranded regions of telomeric DNA. Specifically, the strand replacement method was used to detect G-tails in IMR-90 normal primary human fibroblasts. These telomeres are from fetal lungs and therefore have very long telomeres (approximately 12 kb). High molecular weight (>100 kb) IMR-90 DNA was subjected to the strand replacement reaction and the products were analyzed by I-D alkaline gel electrophoresis (FIG. 12).

Specifically, high molecular weight primary IMR-90 cell DNA was subjected to strand replacement for 5, 10 and 15 minutes and electrophoresed. Alkaline electrophoresis was performed in 0.8–1% agarose with 40 mM NaOH. The gel was prepared with 50 mM NaCl, and 1 mM EDTA, solidified, and soaked in 2 liters of alkaline electrophoretic buffer (40 mM NaOH and 1 mM EDTA). Dried DNA samples were dissolved in alkaline loading buffer (2.5% Ficoll, 50 mM NaOH, 1 mM EDTA, and 0.025% Bromocreosol green), loaded and run at 1 V/cm (250–300 mA) for 12–16 hours at room temperature with buffer circulation. The gel was neutralized by soaking in 1× TBE buffer for 1 hour and vacuum blotted onto the nylon membrane. The material transferred to the membrane was thereafter probed with radioactive TelG. Lanes 1–3 correspond to the reaction with four dNTPs with TelC; lanes 4–6 correspond to reactions with four dNTPs without TelC primer; lanes 7–9 correspond to reactions with three dNTPs with TelC primer; lane 10 contains DNA markers.

Lanes 1–3 show the time course of the reactions with TelC primer and four dNTPs. The rate of $C_s$ synthesis was approximately 250 b/minute. DNA fragments of similar size were synthesized when dGTP was omitted (lanes 7–9), indicating the telomeric origin of the products and the absence of guanine blocks in the terminal 4 kb of the human telomere C-strands. Incorporation of dUTP followed by incubation with dU-glycosylase and alkaline treatment caused loss of the $C_s$ products (not shown). Reactions with equal numbers of human and rat telomeres gave nearly identical amounts of $C_s$ product, even though the rat telomeres are 10 times longer (Makarov, V. L., et al. (1993), Cell 73, 775–787.), consistent with priming only at termini (not shown). These results demonstrate that the strand replacement synthesis with Taq DNA polymerase can proceed in a controlled fashion at least 4 kb along double-stranded native DNA.

Figure 12:
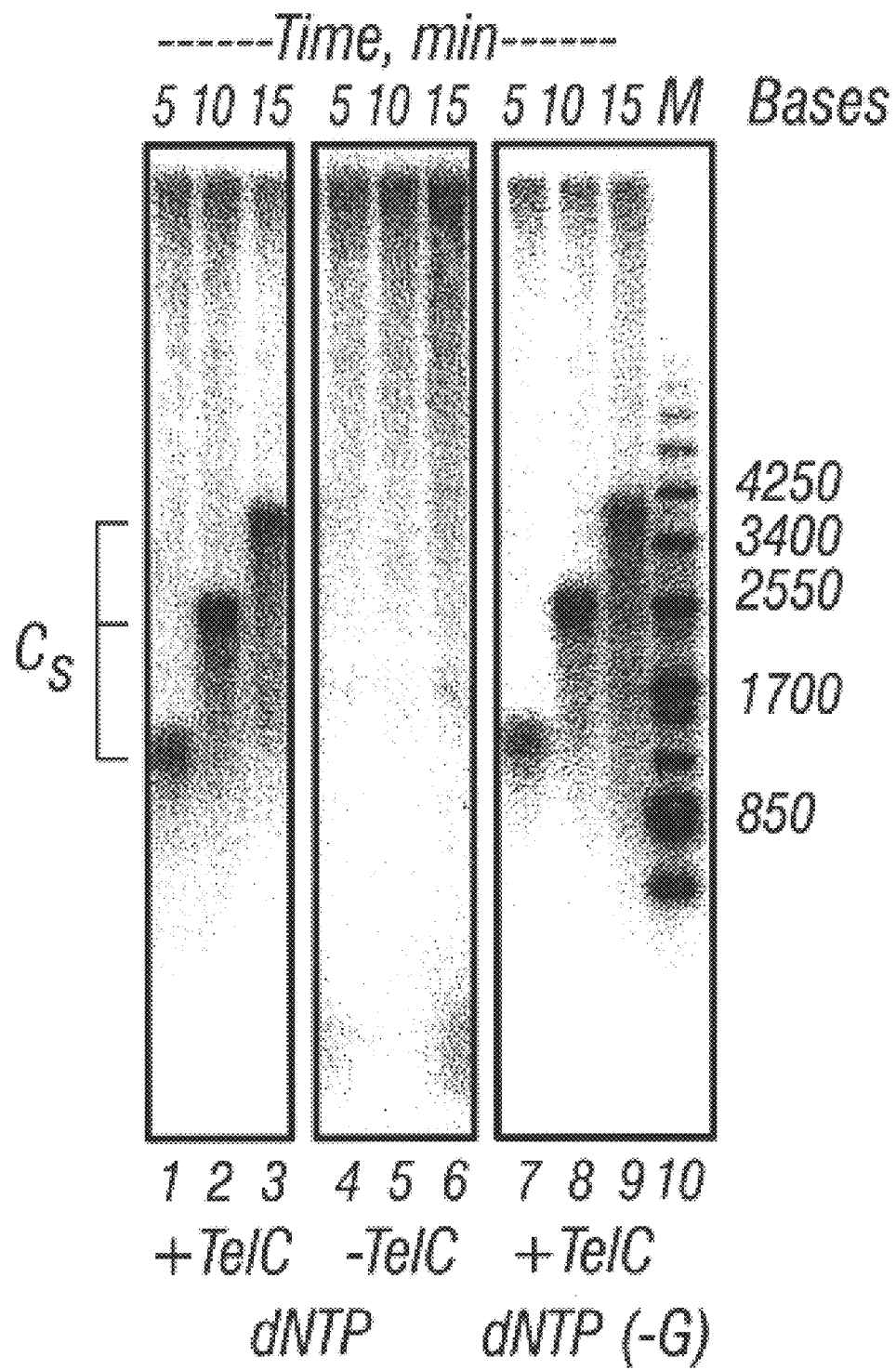
FIG. 12 shows the detection by electrophoresis of naturally-occurring G-rich tails on the human telomeric DNA using one embodiment of the strand replacement method of the present invention.

The results in FIG. 12 are interpreted as synthesis of new DNA strands beginning at the elomere termini. Several alternative explanations can be ruled out. First, no products were generated in the absence of the TelC primer (FIG. 12, lanes 4–6), showing that there are not significant numbers of gaps or nicks in the C-rich strands. Discontinuities in the G-rich strands are ruled out by the fact that the products were of high molecular weight.

To further confirm the nature of the reaction, the naturally occurring G-tails were removed. To remove G-tails 10 mg of IMR-90 DNA was incubated with 300 units/ml S1 nuclease for 15 min at 37° C. in 50 mM NaAc pH 4.5, 1 mM $ZnCl_2$, and 200 mM NaCl, or with 20 units/ml Bal 31 nuclease for 5 min at 30° C. in Bal 31 buffer. For the same purpose, 2 ng of plasmid construct, 10 mg of IMR-90 DNA, or a mixture of the two was incubated with 10 units of T4 DNA polymerase for 10 min at 37° C. in 50 mM Tris-HCl pH 8.8, 15 mM $(NH_4)_2SO_4$, 7 mM $MgCl_2$, 0.1 mM EDTA, 10 mM 2-mercaptoethanol, and 100 µg/ml bovine serum albumin DNA was extracted and resuspended in buffer.

Figures 13A, 13B, 13C:
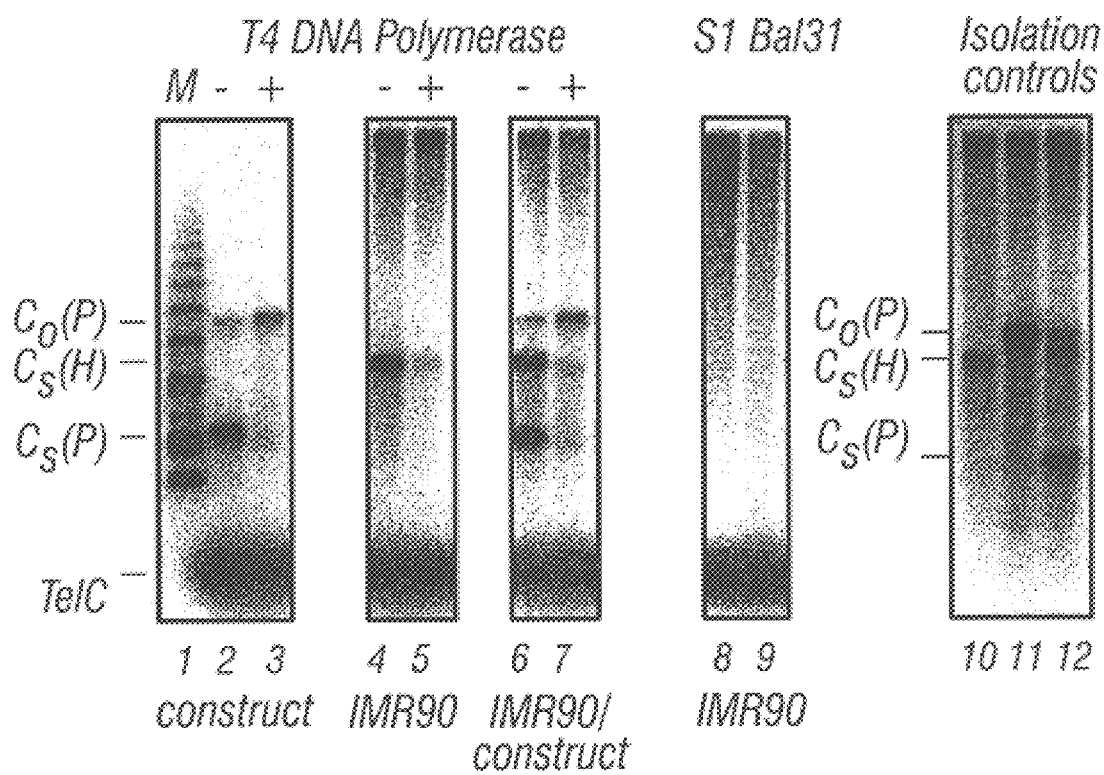
FIGS. 13A through 13C show the products of one embodiment of the strand replacement method analyzed by alkaline agarose electrophoresis and detected by filter hybridization when the naturally-occurring G-rich tails are removed with nuclease.

T4 DNA polymerase trimming reduced the amount of product by more than 10-fold in reactions with (a) the plasmid construct (FIG. 13, lanes 2,3), (b) IMR-90 DNA (lanes 4, 5), or (c) a mixture of IMR-90 DNA and construct (lanes 6,7) ("+" indicates treatment and "−" indicates no treatment). Treatment of IMR-90 DNA with S1 nuclease (FIG. 13, lane 8) or with Bal 31 nuclease (lane 9) completely eliminated the reaction. These data strongly indicate that the strand replacement synthesis requires a 3' G-rich terminus.

G-tails do not seem to be generated or lost during DNA isolation. Concentrations of proteinase K and EDTA were increased during DNA isolation, without effect on the signal (not shown). The isolation protocols were changed in an attempt to test the sensitivity of the assay to formation of unusual secondary structure (e.g., exposure of a G-tail due to strand slippage, or concealment of a G-tail due to formation of G-quartets). Cells and nuclei were incubated with the digestion buffer at 45, 37, and 25° C. to reduce the chance of thermally-induced conformational transition. $K^+$ and $Na^+$ ions were excluded and replaced by $Li^+$ or $Tris^+$ in all isolation steps to reduce the possibility of G-quartet formation. Extractions with phenol and chloroform were replaced by dialysis (not shown) to avoid organic solvents and precipitation. None of the protocols tested had qualitative or quantitative effects on the strand replacement reaction or on non-denaturing hybridization (see below). Thus the assays for G-tails are robust and not sensitive to changes in treatment.

EXAMPLE 3

Strand Replacement Synthesis To Measure The Abundance And Length Of Telomere 3' Overhangs In this example, the strand replacement method of the present invention was combined with non-denaturing hybridization to determine the average lengths of 3' tails in humans. Hinf I digested human DNA, plasmid constructs with 100 b, 170b and 220 b overhangs, or a nearly equimolar (in terms of telomere ends) mixture of human and plasmid DNA were hybridized at 50° C. with 1 $nM^{32}P$-TelC in 20–30 µl of hybridization buffer (50 mM NaCl, 1 mM EDTA and 50 mM Tris-HCl, pH 8.0) for 12–16 h. Some of the samples were subjected to strand replacement (100 mM dNTP, 5 units Taq DNA polymerase; 10 min at 55° C.), then all samples were electrophoresed on a 1% agarose/TAE gel, electroblotted onto a nylon membrane for 16 h and quantitated. The absolute telomere molarity of the IMR90/P04 DNA solution was approximated by spectrophotometry. The molarities of plasmid constructs and telomeres from different human cells were determined by CCD analysis of fluorescence of ethidium bromide stained gels; the signal intensities of plasmids and telomeres were normalized to the signal intensities of a DNA Mass Ladder (GIBCO BRL) and IMR90/P04 DNA, respectively. $^{32}P$-labeled TelC was hybridized under native conditions to the same numbers of human telomeres and control DNA constructs with known lengths of 3' overhangs. The telomeres and constructs were electrophoresed to remove unbound TelC, and the average length of G-tails determined by two independent methods.

Figure 14A:
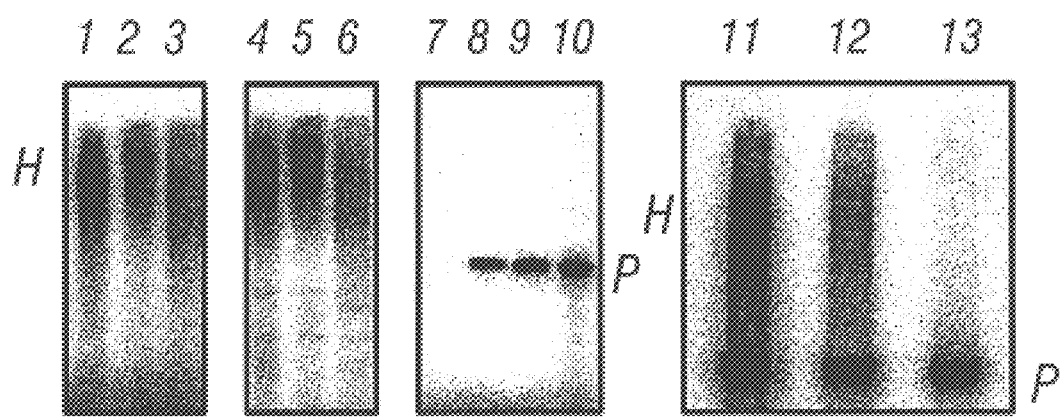
FIG. 14A (Scanned image) is an autoradiogram of DNA samples showing bands coinciding with the telomere terminal restriction fragments found by denaturing hybridization.
Figure 14B:
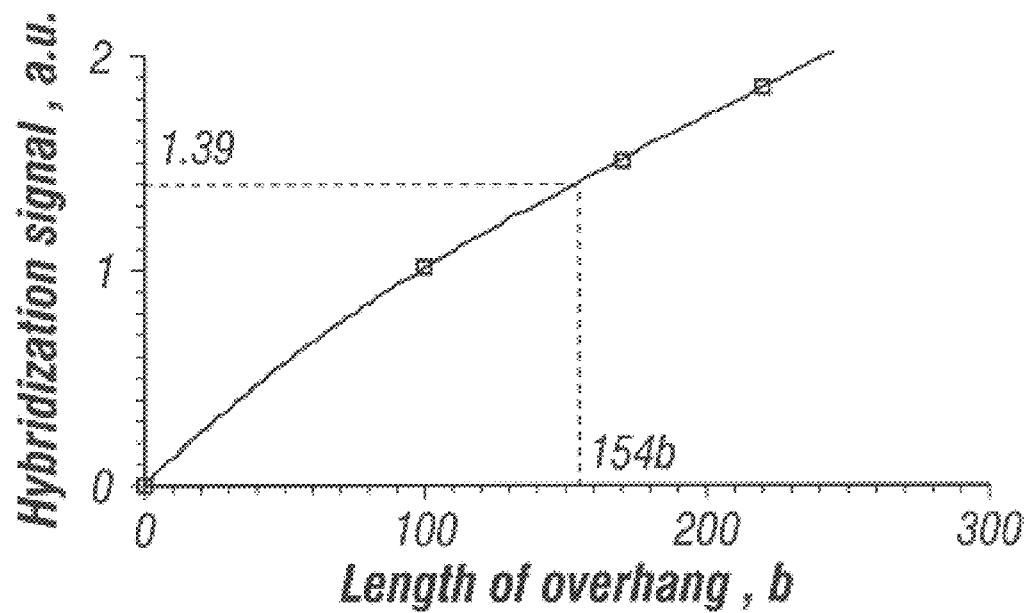
FIG. 14B is a plot of estimated overhang length.

FIG. 14A shows the autoradiogram of DNA samples from blood, HUVE, and primary IMR-90 cells (lanes 1, 2 and 3, respectively), showing broad bands of radioactivity at 10–12 kb, coinciding with the telomere terminal restriction fragments found by denaturing hybridization (lanes 4–6), except for the absence of the sharp bands due to the interstitial (TTAGGG)n tracts. Treatment of the human and construct DNA with S1, mung bean, or Bal 31 nucleases, or with T4 DNA polymerase led to elimination or significant reduction (after T4 polymerase) of the non-denaturing hybridization signal without affecting the size or intensity of the denaturing hybridization signal (not shown). The strength of the TelC hybridization was the same for DNA isolated from both cells and nuclei, prepared by phenol extraction or by only proteinase K/SDS digestion and dialysis. Non-denaturing hybridization with TelG was 20–30 times lower than with TelC for both human and plasmid DNA, consistent with the absence of single-stranded (CCCTAA)n and a very low level of G:G hydrogen bonding (not shown). DNA constructs with (CCCTAA)n overhangs hybridized strongly to TelG and showed no binding to TelC (not shown). The low efficiency of hybridization of telomeres with TelG is strong evidence that the G-tails are covalent extensions (i.e., different lengths of the C- and G-rich strands) rather than conformational extensions (i.e., slippage of the C- and G-rich strands producing G-overhangs and C-loops). FIG. 14A (lanes 7–10) shows how TelC hybridizes to the constructs with plasmid with 100 b overhang. Using the experimental dependence of hybridization upon G-tail length, we calculate that the IMR-90/P04 overhangs were 154 b long (FIG. 14B).

In a separate experiment Tel C was hybridized under non-denaturing conditions to IMR-90/P04, IMR-90/P10, immortal IMR-90, leukocyte, and HUVE cells. The relative amounts of DNA were determined from ethidium bromide fluorescence, and the relative amounts of hybridization by autoradiography. The lengths of the G-tails were between 130 and 210 b long, assuming that the IMR-90/P04 overhangs were 154 b long (Table 3).

The lengths of the IMR90-P04 G-tails were also estimated from the fraction of hybridized TelC that is removed by the strand replacement reaction shown in FIG. 14, lanes 11,12. SR decreased the radioactivity of the human and plasmid DNA by factors of 6.2 and 4.5, respectively, leading one to conclude that the human and plasmid ends bound an average of 6.2 and 4.5 oligonucleotides. Assuming that Tel C saturated the G-tails, the size of the overhangs can be estimated to be 149 in human and 108 bases in the construct. The consistency of these numbers with our earlier results increases our confidence in our estimates of the length and abundance of telomere G-tails.

TABLE 3

Measured Fractions And Lengths Of G-rich Tails In Human And Control DNA

| DNA Sample | Control Plasmid | IMR-90/ P04 | IMR-90/ P10 | IMR-90 Immortal | HUVE | Leukocyte |
| --- | --- | --- | --- | --- | --- | --- |
| Fraction of strands with detectable G-tails[a] | 0.85 (N = 1) | 0.86 ± 0.03 (N = 17) | 0.89 ± 0.03 (N = 4) | 0.88 ± 0.03 (N = 3) | 0.87 ± 0.03 (N = 3) | 0.82 ± 0.05 (N = 3) |
| Average length of G-tail (bases)[b] | 100[c] (108)[d] | 154 (149)[d] | 210 | 130 | 150 | 200 | weight-average G-tail lengths of 0, 100, 170, and 220 b. The TelC hybridization signals were nearly proportional to the average lengths of the G-overhangs (FIG. 14B). Thus, quantitation of the amount of TELC hybridization under these non-denaturing conditions can be used to determine the abundance of single stranded telomere DNA at the ends of chromosomes.

The lengths of the G-tails were first measured by comparing the hybridization signal of TelC to genomic DNA with that of TelC to DNA constructs having G-tails of known lengths. FIG. 14A (lane 11) shows non-denaturing hybridization of Hinf I-digested IMR-90/P04 DNA mixed with an equimolar amount of telomeric ends from the construct with a 100 b G-tail. The hybridization signal of the human DNA was 1.25 times greater than that of the plasmid control. To accurately determine the relative molarity of the human and plasmid overhangs, the same samples were subjected to a 10 min strand replacement reaction (FIG. 14A, lane 12), which should destroy all but the terminal TelC. The relative hybridization signals for the human and plasmid DNA were easily measured, because of the low background in the plasmid-only control (FIG. 14A, lane 13). Assuming that the same number of labeled oligonucleotides remained bound to the ends of the human and plasmid DNA, the molarity of the plasmid ends was 11% greater than that of the human DNA. (This similarity in the estimated molarities of the telomere ends and G-overhangs is consistent with our finding that most or all telomeres have G-tails). Thus, the non-denaturing hybridization signal for the human DNA was 1.39 times greater than to the same number of moles of

EXAMPLE 4

Measuring Telomere Defects

The current method of studying telomere shortening is inaccurate in determining the average length of telomeres, unable to determine the distribution of telomere lengths (particularly the lengths of the shortest telomeres) and is insensitive to defects in the sequences of the telomeric DNA. The present invention provides methods to overcome these limitations. These methods can measure the potential that individuals (particularly those with age-related conditions such as cancer, AIDS, Alzheimers, atherosclerosis, and the progerias) will experience a "telomere crisis" due to telomere shortening, and in predicting or evaluating the efficacy of anti-telomerase therapy or other therapies designed to control telomere function in the treatment of those diseases.

While the successful use of the methods of the present invention does not depend on a precise understanding of the mechanism of telomere shorting, the present invention contemplates that the functional parts of telomeres (see FIG. 15) include regions C and D only, and that exposure of regions A or B to the termini of one or more chromosomes as the result of telomere shortening in normal or precancerous human cells will result in dysfunction of the telomeres, specifically arrest of growth and/or chromosome instability. Evidence that the sequences in region B are not functional comes from studies showing that cells cannot survive with new telomeres made with telomere-like sequences such as (TTGGGG)n and that cell-free extracts are not able to prevent such sequences from non-covalently attaching to each other. Such non-covalent attachments in human cells might lead to the non-clonal telomere associations that characterize the cells of elderly humans and certain human diseases such as ATM and giant cell osteogenic sarcoma. It is critical to directly measure the average and the shortest lengths of region C in human cells and to determine the DNA sequences in region B in order to definitively test the telomere hypothesis of aging and cancer. If the proposed mechanism is correct, such measurements could find clinical applications to test individual humans to accurately measure the rate of telomere shortening or lengthening, predicting future chromosome instabilities, predicting the future behavior of tumor cells or lymphocytes in HIV positive or Alzheimers individuals, and predicting the efficacy of telomere-modifying therapies.

Figure 15:
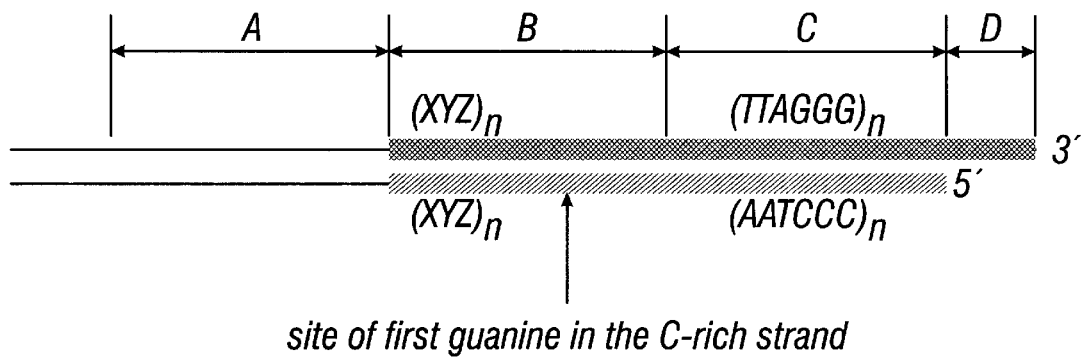
FIG. 15 schematically shows the functional parts of telomeres.

In one embodiment, the steps of the method of the present invention for mapping sequence defects in telomeres comprises: 1) initiation of the synthesis of a new DNA molecule beginning at or near the chromosome terminus, 2) elongation of the synthesis of a new DNA molecule with the repetitive sequence (CCCTAA)n, which is characteristic of a functional vertebrate telomere, and 3) termination of synthesis at an unexpected base, specifically at the first point at which a guanosine is present in the "C-rich strand" within the unique sequence adjacent to the telomeres near the right-most end of fragment A, or within region B (see the arrow in FIG. 15). This mapping reaction has the same basic characteristics of the sequencing reactions, described above, except that termination is achieved when the polymerase is directed to incorporate a guanine into the growing strand, and the analysis is performed by low resolution electrophoresis of high molecular weight DNA product on an agarose gel, as opposed to sequencing which employs single base-resolved electrophoresis on a polyacrylamide gel.

More specifically, when only three natural nucleotides is provided to the polymerase, specifically dATP, dTTP, and dCTP, elongation will proceed unimpeded, copying all of the G-rich strand of the telomeric sequence, (TTAGGG)n. Termination will occur however, the first time that a guanosine appears in the C-rich strand, which will happen within a few bases of unique-sequence DNA, in region A, or perhaps within the telomere-like sequences that might exist in region B (FIG. 15). In other words, elongation will stop only when a specific type of defect occurs in the sequence. When such a cytosine is present the polymerase will be unable to add a new base due to the fact that dGTP is not present in the reaction, or an incorrect base will be incorporated. To optimize the reaction with Taq or to use other enzymes, with proofreading activities, a certain concentration of ddGTP (to be optimized) can be added to the reaction mixture to insure a full stop of elongation.

The length of the synthesized DNA is measured in order to determine how far from the chromosome terminus the termination event has occurred. The advantage of this general technique is that it can determine the total length of regions C+D+(a fraction of region B), without being sensitive to the chromosome-specific variations in the length of regions A and B. The reaction products are electrophoresed on a denaturing alkaline agarose gel to separate them according to molecular weight and detected by standard methods. If a label is incorporated only into the oligonucleotide primer, into the initial few bases of the strand replacement reaction, or into ddGTP, the distribution of number of telomeres of different molecular weights can be determined. This provides a relatively easy means to measure the lengths and abundance of telomeres with very short C+D regions, as might be found in geriatric individuals or in cancer cells.

EXAMPLE 5

Mapping Of Telomere-Like Sequences In Region B

When all 4 dNTPs are present during a DNA polymerase replacement synthesis initiated from the end of chromosomes (as described above) the distance of the polymerase from the end will depend upon reaction time. As longer products are made, they will have 3' ends in regions D, C, B, and then A. There are many ways to use the strand replacement method of the present invention to determine the properties of the telomeric sequences specific distances from the terminus. For example, the strand replacement reaction can be initiated with a variable time of incorporation of dUTP, dGTP, dCTP, and dATP, followed by removal of the dUTP and replacement with dTTP and continuation of the strand replacement reaction for a fixed time. The products are schematically shown in FIG. 16. Subsequently, the uridine bases can be destroyed using deoxyribouridine glycosylase and heat, leaving only the DNA bases added at the end of the reaction, which are different distances from the termini of the chromosomes. This DNA can be hybridized to probes containing (TTAGGG)n and washed at different stringencies to detect whether the DNA has the (TTAGGG)n sequence, or a variant sequence. Alternatively oligonucleotide probes with different sequences can be hybridized to the SR products and washed under stringent conditions to search for specific variant sequences. In principle the products of strand replacement reactions for different times can be combined in the same sample, electrophoresed under denaturing conditions to separate the products according to molecular weight (i.e., with 3' ends located different distances from the chromosome termini), the DNA blotted to filter, the dUTP sites destroyed, and the remaining DNA hybridized to different probes to determine the nature of the DNA sequences different distances from the end. In principle, even single-base variations in the sequences of the glycosylase-resistant fragments could be detected by hybridizing the SR products to labeled telomere sequence oligonucleotides such as $(TTAGGG)_4$, followed by cleavage of the oligonucleotide at any mismatched sites using any one of a number of single-base mutation detection reagents, such as *E. coli* endo IV. The cleaved oligonucleotides can be detected by gel electrophoresis or by loss of energy transfer between fluorescent groups at the ends of the oligonucleotides. This type of reaction lends itself to automation.

In one embodiment, the strand replacement reaction is performed from the beginning in the presence of the 4 normal dNTPs. All that is required is the separation of the SR products from the genomic DNA. As in the previous paragraph, the products of many times of strand replacement can be combined into one sample, which can be separated by molecular weight, hybridized to the oligonucleotide, transferred to a filter, washed to remove unbound oligonucleotides, and cleaved for detection of mismatched bases located at different distances from the ends of the telomeres. Alternatively, the sequence purity at a specific distance from the end can be mapped by detecting variations from the exact 6 base repeat of thymine along the SR product strand. In this assay, after a controlled time of strand replacement in the presence of dCTP, DATP, dGTP, and a controlled ratio of dUTP to dTTP, the nucleotides are removed and replaced with dCTP, dATP, dGTP, and a controlled ratio of dTTP and radioactively- or fluorescently-labeled ddTTP. All SR products would then terminate with a labeled 3' dideoxy thymidine. Degradation of the DNA using deoxyribouridine glycosylase and heat would then terminate the other ends of the products at positions containing thymidine. For reactions terminating in regions of the chromosomes with pure (TTAGGG)n tracts the labeled DNA fragments would form a 6 base ladder on a sequencing gel. For regions with sequence variations that did not retain the perfect 6 base repeat of thymidine, the sequencing gels would exhibit loss of the 6 base ladder. The best method to detect sequence variations within the telomeres will depend upon the nature of the variations found, whether they involve occasional guanines in the 5' strands, non-guanine substitutions for the normal repeat, or variations in the number of bases within some of the repeats. The nature of the actual sequence defects in human telomeres has not been studied in any detail. The methods of mapping of the present invention can be applied to determining the types of sequence defects present within telomeres in normal and abnormal human cells. For example, the DNA synthesized different distances from the ends of telomeres can be cloned and sequenced by standard methods to discover the actual sequence variants present.

EXAMPLE 6

Sequencing Double-Stranded DNA Using ddNTP-Terminated Strand Replacement Reaction A strand replacement sequencing reaction was performed on a linear, double-stranded plasmid template using Taq polymerase, $^{32}$P radioactively labels, and polyacrylamide electrophoresis. The experiment involved a) DNA preparation, b) strand replacement, c) and gel electrophoresis.

A) DNA Preparation

40 μg of plasmid pUC19 (New England Biolabs) was digested 2.5 h at 37° C. with 200 units of Bam H1 (Boehringer Mannheim Biochemicals, "BMB") in 200 ul of 0.1× BMB "restriction buffer B." The fraction of linearized plasmid was checked by electrophoresing 2 μl of the restricted DNA solution on a 1% agarose gel. The termini of the restricted plasmid were dephosphorylated in a 30 min reaction at 37° C. with 188 μl of the restricted DNA (39.5 μg), 23 μl of 10× alkaline phosphatase buffer (BMB), 5 μl of shrimp alkaline phosphatase (BMB), and 2 μl H$_2$O. The solution was then heated to 70° C. for 15 min to inactivate the alkaline phosphatase. The DNA was precipitated by adding 5 μl glycogen (10 μg/μl), 23 μl 3 M sodium acetate (pH 5.2), and 2.5 volumes 100% ethanol, and stored overnight at −70° C. The DNA was pelleted 15 min at 13,000 g and the pellet washed twice with cold 70% ethanol. The DNA was resuspended in 70 μl H$_2$O.

The DNA in 67.8 μl was mixed with 7.2 μl of double-stranded adaptor oligonucleotide (25 pmol/μl), 20 μl of 5× ligation buffer (BMB), and 5 μl (1 unit/μl) T4 DNA ligase (BMB). The ligation reaction took place overnight at 14–16° C. The ligase was inactivated at 70° C. for 15 min. The ligation substrates and products had the following structure:

```
Before ligation:

pUC19                  Bam HI - Adaptor
5'------------GTACCCGGG-OH    P-GATCGACGAUACCGUGGACCUCGTTTTT
3'oh 3'------------CATGGGCCCCTAG-OH
OH-TGCTATGGCACCTGGAGCAAAA 5'OH After ligation:

5'------------GTACCCGGGGATCGACGAUACCGUGGACCUCGTTTTT 3' OH
3'------------CATGGGCCCCTAG TGCTATGGCACCTGGAGCAAAA 5' OH
```

*1 nucleotide gap

After ligation, 98 μl (39 μg) pUC19 was digested for 2.5 h at 37° C. with 16 μl (10 units/μl) Pst I, 30 μl buffer H (buffer H from BMB), and 156 μl H$_2$O, in order to remove the adaptor oligonucleotide from one end of the molecule. This insured that the strand replacement reaction would initiate at one end of the template. Aliquots of the DNA were analyzed to insure that ligation and restriction had been complete. The 2.7 kb ligated BamHI/Pst I pUC19 fragment was purified on 1% low melting agarose. The gel band (1.6 ml) was excised from the gel and incubated for 10 min at 65° C., and then incubated with 2 h at 45° C. with 10 μl agarase (1 unit/μl), 66 μl 25× agarase buffer (BMB). The sample was mixed with 166 μl of 3 M sodium acetate (pH5.2), mixed, and spin at 13,000 g for 10 minutes. The supernatant was spun a second time for 10 min and the DNA extracted with phenol/chloroform once and chloroform twice. DNA was precipitated as above and suspended in 40 μl H$_2$O. Final yield was 15 μg DNA.

B) Strand Replacement

Two protocols were used for the SR sequencing reactions. The solutions and reagents for the sequencing reactions were as follows:

Buffers:
  Buffer A: 100 mM Tris HCl, pH 8.0, 100 mM MgCl2.
  Buffer B: 500 mM Tris HCl, pH 8.9, 100 mM KCl, 25 mM MgCl2.

Labeling Mix:
  10 uM dGTP, 5 uM dCTP, 5 uM dTTP, 10 uM Tris HCl, pH 8.0.

Polymerization/Termination Mixes:
  G-terminating mix: 30 μM dNTP; 0.25 mM ddGTP; 0.37 MM MgCl$_2$.
  A-terminating mix: 30 μM dNTP; 1.0 mM ddATP; 1.12 MM MgCl$_2$.
  T-terminating mix: 30 μM dNTP; 1.5 mM ddTTP; 1.62 mM MgCl$_2$.
  C-terminating mix: 30 μM dNTP; 0.5 mM ddCTP; 0.62 mM MgCl$_2$.
  [where 30 μM dNTP: 30 μM of each of dGTP, dCTP, dATP and dTTP].

Labeling Solution:
  $^{32}$P-dATP solution: 2 μl $^{32}$P-dATP [3000 Ci/mmol (3.3 μM), Amersham], 2 μl 10 uM dATP, 1 μl 50 mM Tris HCl, pH 8.0.

Taq DNA Polymerase Dilution Buffer:
  10 mM Tris HCl, pH 8.3, 50 mM KCl, 0.5% Tween 20, 0.5% Nonidet P40.

Figure 17:
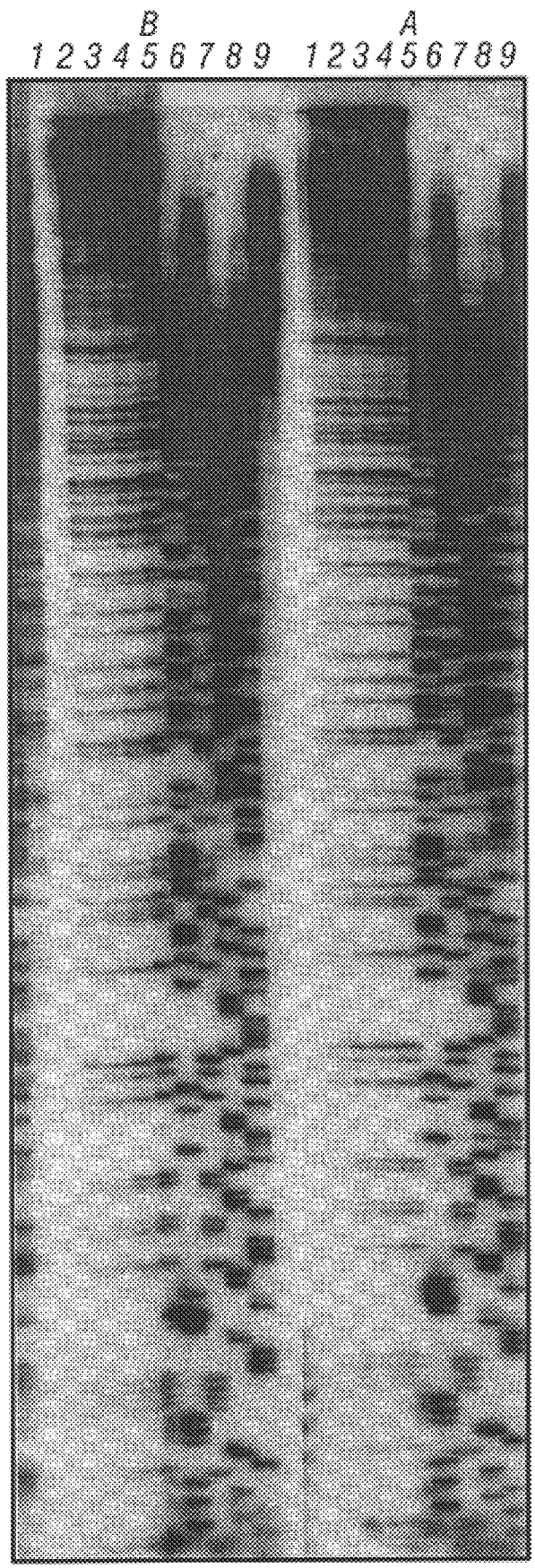
FIG. 17 (Scanned images) shows the sequencing gel results following strand replacement performed according to the present invention.

Stop/Loading Solution:
  95% formamide, 20 mM EDTA, 0.05% Bromphenol Blue, 0.05% Xylene Cyanol.
Taq DNA Polymerase:
  AmpliTaq, Cat.# N801-0060, PERKIN ELMER.
Nucleotides:
  GeneAmp dNTPs, 10 mM, Cat.# N808-0007, PERKIN ELMER ddNTPs, Cat.# 775 304, BOEHRINGER MANNHEIM.
First Protocol:
  Sequencing using 32P-a-dATP incorporation to label.
Addition Of Fresh Primer:
  To insure that all the strands were bound to primer, the DNA was hybridized under non-denaturing conditions to the primer oligonucleotide 5'AAAACGAGGTCCACGG-TATCGT 3'. To do this 0.2 pmol pUC19 DNA (0.17 pmol/$\mu$l or 0.3 $\mu$g/$\mu$l) was added to 0.4 pmol primer (0.1 pmol/$\mu$l), 1 $\mu$l Buffer A or 2 $\mu$l of Buffer B, and H$_2$O to make a total of 10 $\mu$l. The mixture was heated at 65° C. for 5 min, then at 37° C. for 30 min.
Labeling Reaction:
  To one tube was added 2 $\mu$l of the labeling mix, 2 $\mu$l of the $^{32}$P-dATP mix, 1 $\mu$l Taq DNA polymerase (diluted 2 times with Taq dilution buffer), and 5 $\mu$l H$_2$O. The mixture was incubated at 37° C. 5 $\mu$l aliquotes were taken after 1 min, 2 min, 5 min, and 10 min of the labeling reaction.
Termination Reaction:
  2 $\mu$l of the "A"-terminating mix were added to 4 $\mu$l of labeled DNA (after 1, 2, 5 and 10 min reaction) in a 0.5 ml tube, covered with mineral oil and incubated at 55° C. for 10 min. The reaction was stopped by adding 4 $\mu$l of the Stop/Loading solution. Samples were heated at 95° C. for 3 min, cooled at 4° C. and loaded on the sequencing gel.
Second Protocol:
  Sequencing using kinase 32P-labeled primer.
Hybridization Step:
  Prior to initiating strand replacement, a mix was made comprising 3 $\mu$l pUC19 DNA (0.5 pmol), 2 $\mu$l of $^{32}$P-kinase labeled primer (1 pmol), 1 $\mu$l Buffer A or 3 $\mu$l Buffer B, 9 $\mu$l 10 mM Tris HCl, pH 8.0 (if Buffer A) or 11 $\mu$l H$_2$O (if Buffer B). The mixture was heated at 65° C. for 5 min, and then at 37° C. for 30 minutes.
Strand Replacement:
  To initiate strand replacement, 1 $\mu$l of Taq DNA polymerase (diluted 2 times with the dilution buffer) was added to the mixture at room temperature to create a second mixture. Thereafter, the following solution were added to 4 $\mu$l of this second mixture:
  2 $\mu$l of the "G-terminating mix" ("G"-tube);
  2 $\mu$l of the "A-terminating mix" ("A"-tube);
  2 $\mu$l of the "T-terminating mix" ("T"-tube);
  2 $\mu$l of the "C-terminating mix" ("C"-tube); and
  2 $\mu$l of the 30 mM dNTP mix ("dNTP"-tube).
The "G", "A", "T", "C" and "dNTP"-tubes were incubated at 55° C. for 10 minutes. The reaction was stopped by adding 4 $\mu$l of the Stop/Loading solution, and the reaction was heated at 95° C. for 3 minutes, cooled at 4° C., and loaded on sequencing gel.
  C) Gel Electrophoresis
  A standard denaturing 6% polyacrylamide sequencing gel was run under standard conditions (Current Protocols in Molecular Biology, eds. Ausubel, F. M., Brent, R., Kingston, R. E., Moore, D. D., Seidman, J. G., Smith, J. A., Struhl, K., Vol. 1, Supplement 16, 1991). The $^{32}$P-labeled SR products were detected by autoradiography on film, exposed ~8 h at room temperature. FIG. 17 is an image of the autoradiogram.

Left panel ("B") represents the reactions performed in buffer B. Lanes 1–4 represent DNA labeled with $^{32}$P dATP for 1 min, 2min, 5 min, and 10 min, respectively. Each of these reactions incorporated ddATP. The bands are at the positions expected for adenines in the pUC19 sequence. Very little background is found between bands and the bands have uniform intensity. At this ratio of ddATP to DATP, the strand replacement reaction continued on to high molecular weight, beyond the resolution of the gel. Lanes 5–8 correspond to DNA labeled using kinase-labeled primer from different termination tubes, "G-tube", "A-tube", "T-tube", and "C-tube", respectively. Each of these lanes had bands corresponding to ddNTP termination at the cognate base position in the double-stranded template DNA. The ddNTP mixes have not been optimized to give the same radioactivity in each lane, however all lanes show termination at the ddNTP sites without detectable background between lanes due to premature termination of the SR sequencing reaction. Band intensities are very uniform from site to site within lanes, except where bands overlap due to homopolymeric tracts. Lane 9 corresponds to DNA labeled using kinase-labeled primer in the reaction of the "DNTP tube." This reaction shows no termination of the strand replacement reaction at low molecular weights, illustrating lack of detectable premature termination of the product. Right panel ("A") represents the same reactions seen in the left panel, with the exception that the reactions were run in buffer A. Under these conditions there are detectable amounts of premature termination, even in lane 9, which represented the "dntp tube." Thus the strand replacement synthesis from a double-stranded template can be used to sequence DNA.

What is claimed is:

1. A method for sequencing nucleic acid, comprising:
  a) providing:
    i) substantially double-stranded nucleic acid template,
    ii) a polymerase having synthetic activity and a 5'-3' exonuclease activity,
    iii) one or more nucleic acid precursors, and
    iv) one or more terminating agents;
  b) mixing said polymerase, said one or more precursors, said one or more terminating agents and said template under conditions such that nucleic acid synthesis takes place for a reaction period during which said template remains substantially double-stranded and nucleic acid product is created containing said one or more terminating agents; and
  c) detecting said product of said reaction under conditions whereby the nucleic acid sequence of at least a portion of said template is revealed.

2. The method of claim 1, wherein said substantially double-stranded template comprises a single-stranded region.

3. The method of claim 2, wherein a primer is added to said reaction of step (b), said primer capable of hybridizing to said single-stranded region of said substantially double-stranded template.

4. The method of claim 1, wherein prior to step (b) one strand of said substantially double-stranded template is nicked.

5. The method of claim 1, wherein said one or more nucleic acid precursors mixed in step (b) are selected from the group consisting of dATP, dGTP, dTTP and dCTP.

6. The method of claim 1, wherein said one or more terminating agents mixed in step (b) are selected from the group consisting of ddATP, ddGTP, ddTTP and ddCTP.

7. The method of claim 1, wherein said polymerase is Taq DNA polymerase.

8. The method of claim 1, wherein said polymerase is *E. coli* DNA polymerase I.

9. The method of claim 1, wherein said detecting comprises gel electrophoresis.

10. A method for sequencing nucleic acid, comprising:
   a) providing:
      i) substantially double-stranded nucleic acid template,
      ii) an endonuclease capable of specifically nicking one of the strands of said double-stranded nucleic acid template,
      iii) a polymerase having synthetic activity and a 5'-3' exonuclease activity,
      iv) one or more nucleic acid precursors, and
      v) one or more terminating agents;
   b) mixing said substantially double-stranded template with said endonuclease under conditions such that a substantially double-stranded template is produced containing a nick on one strand;
   c) adding a solution to said nicked template, said solution comprising said polymerase, said one or more precursors, and said one or more terminating agents, whereby said adding is carried out under conditions such that nucleic acid synthesis takes place for a reaction period during which said template remains substantially double-stranded and nucleic acid product is created containing said one or more terminating agents; and
   d) detecting said product of said reaction under conditions whereby the nucleic acid sequence of at least a portion of said template is revealed.

11. The method of claim 10, wherein said endonuclease is f1 gpII.

12. The method of claim 10, wherein said one or more nucleic acid precursors mixed in step (b) are selected from the group consisting of dATP, dGTP, dTTP and dCTP.

13. The method of claim 12, wherein one of said one or more nucleic acid precursors are labeled.

14. The method of claim 10, wherein said one or more terminating agents mixed in step (b) are selected from the group consisting of ddATP, ddGTP, ddTTP and ddCTP.

15. The method of claim 14, wherein one of said one ore more terminating agents are labeled.

16. The method of claim 13, wherein said label is selected from the group consisting of radiolabels and fluorescent labels.

17. The method of claim 16, wherein said label is $^{32}$P.

18. The method of claim 17, wherein said detecting comprises gel electrophoresis and autoradiography.

19. A method for sequencing nucleic acid, comprising:
   a) providing:
      i) substantially double-stranded nucleic acid template, said substantially double-stranded template comprising a single-stranded region,
      ii) a polymerase having synthetic activity and a 5'-3' exonuclease activity,
      iii) one or more nucleic acid precursors,
      iv) one or more terminating agents, and
      v) a primer capable of hybridizing to said single-stranded region of said substantially double-stranded template;
   b) mixing said polymerase, said one or more precursors, said one or more terminating agents, said primer and said template under conditions such that nucleic acid synthesis takes place for a reaction period during which said template remains substantially double-stranded and nucleic acid product is created containing said one or more terminating agents; and
   c) detecting said product of said reaction under conditions whereby the nucleic acid sequence of at least a portion of said template is revealed.

20. The method of claim 16, wherein said template is telomeric DNA.

21. The method of claim 17, wherein said primer comprises the sequence CCCUAA.

* * * * *

UNITED STATES PATENT AND TRADEMARK OFFICE
CERTIFICATE OF CORRECTION

PATENT NO. : 6,117,634
DATED : September 12, 2000
INVENTOR(S) : Langmore et al.

It is certified that error appears in the above-identified patent and that said Letters Patent is hereby corrected as shown below:

On the title page, item [75], inventors, please delete "Markarov" and insert --Makarov-- therefor.

On the front page, item [22], please change the filing date from "Mar. 6, 1997" to -- Mar. 5, 1997 -- therefor.

In claim 1, column 38, line 42, after "acid synthesis", please insert -- via strand replacement -- therefor.

In claim 10, column 39, line 23, after "acid synthesis", please insert -- via strand replacement -- therefor.

In claim 19, column 40, line 26, after "acid synthesis", please insert -- via strand replacement -- therefor.

Signed and Sealed this

First Day of May, 2001

*Attest:*

NICHOLAS P. GODICI

*Attesting Officer*   *Acting Director of the United States Patent and Trademark Office*